United States Patent [19]

Takaya et al.

[11] Patent Number: 4,544,751
[45] Date of Patent: Oct. 1, 1985

[54] THIADIAZOLE DERIVATIVES

[75] Inventors: Takao Takaya, Sakai; Hisashi Takasugi, Kohamanishi; Toshiyuki Chiba, Nara; Zenzaburo Tozuka, Toyonaka, all of Japan

[73] Assignee: Fujisawa Pharmaceutical Co., Ltd., Osaka, Japan

[21] Appl. No.: 396,643

[22] Filed: Jul. 9, 1982

Related U.S. Application Data

[60] Division of Ser. No. 206,299, Nov. 12, 1980, Pat. No. 4,350,693, which is a division of Ser. No. 26,779, Apr. 3, 1979, Pat. No. 4,263,291, which is a continuation-in-part of Ser. No. 839,974, Oct. 6, 1977, abandoned.

[30] Foreign Application Priority Data

Oct. 8, 1976 [GB] United Kingdom ............... 42057/76

[51] Int. Cl.$^4$ ................. C07D 285/06; C07D 285/12; A61K 31/425
[52] U.S. Cl. .................... 548/127; 548/203; 548/204; 548/134; 548/136; 544/26; 544/27
[58] Field of Search ............... 548/203, 204, 127, 134, 548/136; 544/26, 27, 21; 424/246

[56] References Cited

U.S. PATENT DOCUMENTS 3,971,778 7/1976 Cook et al. ..................... 260/243 C
4,331,665 5/1982 Teraji ..................... 544/27
4,332,798 6/1982 Teraji et al. ..................... 544/27

Primary Examiner—Nicholas S. Rizzo
Attorney, Agent, or Firm—Dayton R. Stemple

[57] ABSTRACT 3,7-disubstituted-3-cephem-4-carboxylic acid compounds having bacteriostatic properties and the following formula:

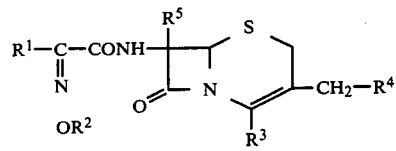

in which $R^1$ is thiadiazolyl or isothiazolyl, each of which may have suitable substituent(s), or thiazolyl; $R^2$ is hydrogen or lower alkyl; $R^3$ is carboxy or protected carboxy; $R^4$ is hydrogen, acyloxy or a heterocyclicthio group which may have suitable substituent(s); and $R^5$ is hydrogen or lower alkoxy, process for making same and treating infectious diseases therewith.

3 Claims, No Drawings

THIADIAZOLE DERIVATIVES

This is a division, of application Ser. No. 206,299, filed Nov. 12, 1980, now U.S. Pat. No. 4,350,693, which in turn was a division of Ser. No. 26,779, filed Apr. 3, 1979, now U.S. Pat. No. 4,263,291, which in turn was a continuation-in-part of Ser. No. 839,974, filed Oct. 6, 1977, now abandoned.

The present invention relates to new 3,7-disubstituted-3-cephem-4-carboxylic acid compounds and pharmaceutically acceptable salts thereof. More particularly, it relates to new 3,7-disubstituted-3-cephem-4-carboxylic acid compounds and pharmaceutically acceptable salts thereof which have antimicrobial activites and to processes for the preparation thereof, to pharmaceutical composition comprising the same, and to a method of using the same therapeutically for treatment of infectious diseases in human being and animals.

Accordingly, it is one object of the present invention to provide 3,7-disubstituted-3-cephem-4-carboxylic acid compounds and pharmaceutically acceptable salts thereof, which are highly active against a number of pathogenic microorganisms.

Another object of the present invention is to provide processes for the preparation of 3,7-disubstituted-3-cephem-4-carboxylic acid compounds and pharmaceutically acceptable salts thereof.

A further object of the present invention is to provide pharmaceutical composition comprising, as active ingredients, said 3,7-disubstituted-3-cephem-4-carboxylic acid compounds and pharmaceutically acceptable salts thereof.

Still further object of the present invention is to provide a method for treatment of infectious diseases caused by pathogenic bacteria in human being and animals.

The object 3,7-disubstituted-3-cephem-4-carboxylic acid compounds are novel and can be represented by the following general formula (I):

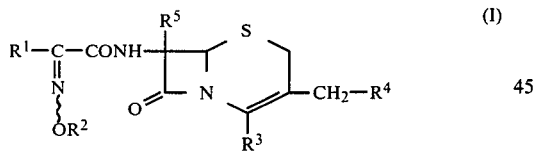

in which
R$^1$ is thiadiazolyl or isothiazolyl, each of which may have suitable substituent(s), or thiazolyl;
R$^2$ is hydrogen or lower alkyl;
R$^3$ is carboxy or protected carboxy;
R$^4$ is hydrogen, acyloxy or a heterocyclicthio group which may have suitable substituent(s); and
R$^5$ is hydrogen or lower alkoxy.

The 3,7-disubstituted-3-cephem-4-carboxylic-acid compounds (I) can be prepared by conventional processes applied in the cephalosporin field as illustrated by the following scheme.

Process 1

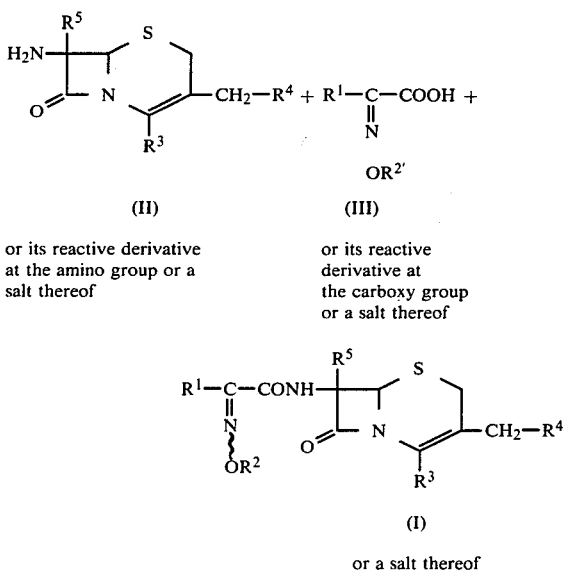

Process 2

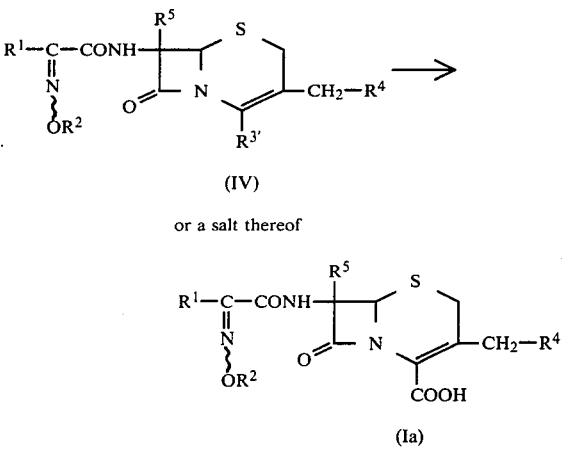

wherein R$^1$, R$^2$, R$^3$, R$^4$ and R$^5$ are each as defined above; R$^{2'}$ is hydrogen, lower alkyl or a hydroxy protective group; and R$^{3'}$ is protected carboxy.

The starting compounds (III) and (IV) are novel and can be prepared by the processes as illustrated by the following scheme.

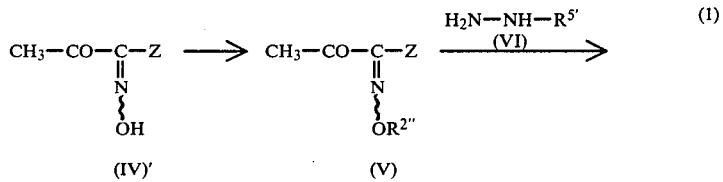

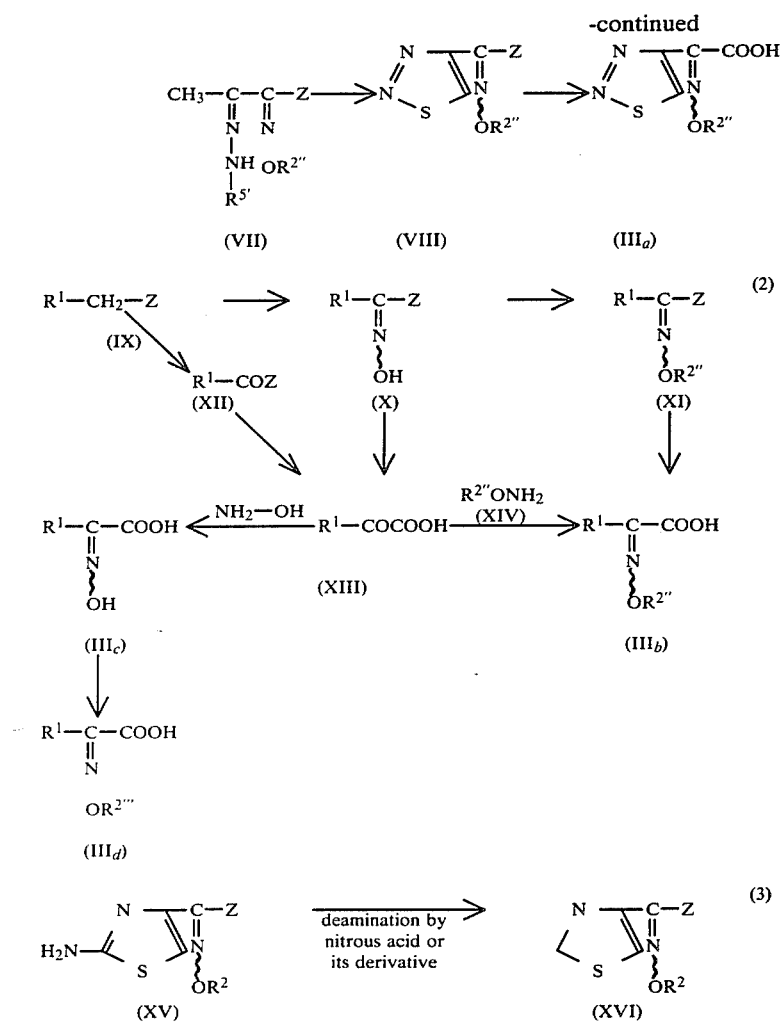

in which $R^1$ and $R^2$ are each as defined above;
$R^{2''}$ is lower alkyl;
$R^{2'''}$ is a hydroxy protective group;
$R^{5'}$ is an amino protective group; and
Z is protected carboxy.

The starting compound (IV) can be prepared by the Process 1 as illustrated above.

In the present invention, with regard to the object compounds (I) and (Ia), the starting compounds (III), (IIIa)–(IIId) and (IV) and the other compounds (IV), (V), (VII), (VIII), (X),(XI),(XV) and (XVI), it is to be understood that all of said compounds include syn isomer, anti isomer and a mixture thereof. And, as to the object compounds (I) and (Ia), the syn isomer thereof means one geometrical isomer having the group represented by the following formula:

$$R^1-\underset{N-OR^2}{\overset{\|}{C}}-CO-$$

and the anti isomer means the other geometrical isomer having the group of the formula:

$$R^1-\underset{R^2O-N}{\overset{\|}{C}}-CO-$$

wherein $R^1$ and $R^2$ are each as defined above.

Further, as to the starting compounds and the other compounds, the syn and anti isomers thereof also are represented by the same geometrical configuration as that of the object compound, respectively.

Suitable pharmaceutically acceptable salt of the object 3,7-disubstituted-3-cephem-4-carboxylic acid compounds (I) are conventional non-toxic salts and may include a metal salt such as an alkali metal salt (e.g., sodium salt, potassium salt, etc.) and an alkaline earth metal salt (e.g., calcium salt, magnesium salt, etc.), ammonium salt, an organic amine salt (e.g., trimethylamine salt, triethylamine salt, pyridine salt, picoline salt, dicyclohexylamine salt, N,N'-dibenzylethylenediamine salt, diethanolamine salt, etc.), an organic acid salt (e.g., maleate, lactate, tartrate, methanesulfonate, benzenesulfonate, toluenesulfonete etc.), an inorganic acid salt (e.g., hydrochloride, hydrobromide, sulfate, phosphate, etc.), or a salt with an amino acid (e.g., arginine, aspartic acid, lysine, glutamic acid, etc.), and the like.

In the above and subsequent description of the present specification, suitable examples and illustrations for the various definitions to be included within the scope thereof are explained in details as follows.

The term "lower" is intended to mean 1 to 6 carbon atom(s) unless otherwise provided.

Suitable thiadiazolyl may include 1,2,3-thiadiazolyl, 1,2,4-thiadiazolyl, 1,2,5-thiadiazolyl and 1,3,4-thiadiazolyl.

Said thiadiazolyl and isothiazolyl for $R^1$ may have one or two suitable substituent(s) such as lower alkyl, halogen, hydroxy, amino, protected amino or the like.

Suitable protected amino may include an acylamino, and an amino protected by a conventional protective group other than the acyl group such as benzyl, diphenylmethyl, trityl or the like.

Suitable lower alkyl may include methyl, ethyl, propyl, isopropyl, butyl, isobutyl, tert-butyl, pentyl, hexyl and the like, and preferably one having 1 to 4 carbon atom(s), and more preferably one having 1 to 2 carbon atom(s).

Suitable halogen may include chlorine, bromine, fluorine and iodine.

Suitable protected carboxy and include esterified carboxy in which said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.); lower alkenylester (e.g., vinyl ester, alkyl ester etc.); lower alkynyl ester (e.g., ethynyl ester, propynyl ester, etc.); mono(or di or tri)-halo(lower)alkyl ester (e.g., 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, etc.); lower alkanesulfonyl(lower)alkyl ester (e.g., 2-mesylethyl ester etc.); ar(lower)alkyl ester, preferably mono(or di or tri)phenyl(lower)alkyl ester which may have one or more suitable substituent(s) (e.g., benzyl ester, 4-methoxybenzyl ester, 4-nitrobenzyl ester, phenethyl ester, trityl ester, diphenylmethyl ester, diphenylethyl ester, bis(methoxyphenyl)methyl ester, 3,4-dimethoxybenzyl ester, 4-hydroxy-3,5-ditertiarybutylbenzyl ester, etc.); aryl ester which may have one or more suitable substituent(s) (e.g., phenyl ester, tolyl ester, tertiarybutylphenyl ester, xylyl estor, mesityl ester, cumenyl ester, etc.), and the like.

Preferable example of protected carboxy may be, more concretely, lower alkoxycarbonyl having 2 to 7 carbon atoms (e.g., methoxycarbonyl, ethoxycarbonyl, propoxycarbonyl, isopropoxycarbonyl, butoxycarbonyl, isobutoxycarbonyl, t-butoxycarbonyl, pentyloxycarbonyl, t-pentyloxycarbonyl, hexyloxycarbonyl, 1-cyclopropylethoxycarbonyl, etc.), and preferably one having 2 to 4 carbon atoms; or diphenyl(lower) alkoxycarbonyl having $C_{14}$ to $C_{19}$ carbon atoms (e.g., diphenylmethoxycarbonyl, diphenylethoxycarbonyl, etc.), and preferably one having $C_{14}$ to $C_{16}$ carbon atoms.

Suitable acyl moiety in the terms "acylamino" and "acyloxy" as mentioned above may include carbamoyl in which the amino function may be protected, aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, etc.), and preferably one having 1 to 3 carbon atom(s); lower alkoxycarbonyl (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), and preferably one having 2 to 5 carbon atoms; lower alkanesulfonyl (e.g., mesyl, ethanesulfonyl, propanesulfonyl, isopropanesulfonyl, butanesulfonyl, etc.); arenesulfonyl (e.g., benzenesulfonyl, tosyl, etc.); aroyl (e.g., benzoyl, toluoyl, naphthoyl, phthaloyl, indancarbonyl, etc.); ar(lower)alkanoyl (e.g., phenylacetyl, etc.), and the like. The acyl moiety as stated above may have one or two suitable substituent(s) such as halogen (e.g., chlorine, bromine, iodine or fluorine), hydroxy, cyano, nitro, lower alkoxy (e.g., methoxy, ethoxy, propoxy, isopropoxy, etc.); lower alkyl (e.g., methyl ethyl, propyl isopropyl, butyl, etc.), lower alkenyl (e.g., vinyl, allyl etc.), aryl (e.g., phenyl, tolyl, etc.) or the like.

Suitable example of the acyl having such substituent(s) may preferably be halo(lower)alkanoyl (e.g., chloroacetyl, dichloroacetyl, trichloroacetyl, trifuoroacetyl, etc.), more preferably one having 2 to 3 carbon atoms, and the like. Suitable protective group for amino in the above acyl moiety (e.g. carbamoyl) may preferably be, for example, acyl such as halo(lower)alkanoyl (e.g., chloroacetyl, dichloroacetyl, trichloroacetyl, trifluoroacetyl, etc.) or the like.

Suitable heterocyclic moiety in the term "a heterocyclicthio group which may have suitable substituent(s)" means saturated or unsaturated, monocyclic or polycylic heterocyclic group containing at least one heteroatom such as an oxygen, sulfur, nitrogen atom and the like. And, especially preferable heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc; saturated 3 to 8-membered heteromonocyclic group containing 1 to 4 nitrogen atom(s), for example, pyrrolidinyl, imidazolidinyl, piperidino, piperazinyl, etc.; unsaturated condensed heterocyclic group containing 1 to 4 nitrogen atom(s), for example, indolyl, isoindolyl, indolizynyl, benzimidazolyl, quinolyl, isoquinolyl, idazolyl, benzotriazolyl, etc.; unsaturated 3- to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.) etc.; saturated 3 to 8-membered heteromonocyclic group containing 1 to 2 oxygen atom(s) and 1 to 3 nitrogen atom(s), for example, morpholinyl, etc.; unsaturated condensed heterocyclic group containing 1 to 2 oxygen atom(s) and 1 to 5 nitrogen atom(s), for example benzoxazolyl, benzoxadiazolyl, etc.; unsaturated 3 to 8-membered heteromonocyclic group containing 1 to 2 sulfur atom(s) and 1 to 3 nitrogen atom(s), for example thiazolyl, thiadiazolyl (e.g., 1,2,4-thiadiazolyl, 1,3,4-thiadiazolyl, 1,2,5-thiadiazolyl, etc.), etc; saturated 3 to 8-membered heteromonocyclic group containing 1 to 2 sulfur atom(s) and 1 to 3 nitrogen atom(s), for example, thiazolidinyl, etc.; unsaturated 3 to 8 membembered heteromonocyclic group containing a sulfur atom, for example, thienyl, etc.; unsaturated condensed heterocyclic group containing 1 to 2 sulfur atom(s) and 1 to 3 nitrogen atom(s), for example, benzothiazolyl, benzothiadiazolyl, etc. and the like; wherein said heterocyclic group may have one or two suitable substituent(s) such as lower alkyl (e.g., methyl, ethyl, propyl, isopropyl, butyl, isobutyl, pentyl, cyclopentyl, hexyl, cyclohexyl, etc.); lower alkenyl (e.g., vinyl, allyl, butenyl, etc.); aryl (e.g., phenyl, tolyl, etc.); halogen (e.g., chlorine, bromine, iodine or fluorine); amino, di(lower)alkylamino(-lower)alkyl(e.g.,dimethylaminomethyl,dimethylaminoethyl,diethylaminopropyl, diethylaminobutyl, etc.); or the like.

Suitable "hydroxy- and amino protective groups" may preferably be acyl moiety as exemplified above, respectively.

Suitable "lower alkoxy" may include methoxy, ethoxy, propoxy, isopropoxy, butoxy, isobutoxy, t-butoxy, pentyloxy, hexyloxy and the like, preferably one having 1 to 4 carbon atom(s), and more preferably one having 1 to 2 carbon atom(s).

Preferred embodiments of the object compound (I) are as follows.

Preferred embodiment of $R^1$ is thiadiazolyl (more preferably 1,2,3-thiadiazolyl, 1,2,5-thiadiazolyl, 1,3,4-thiadiazolyl, etc.), which may have lower alkyl (preferably methyl, ethyl, etc.), or isothiazolyl; or thiazolyl; the preferred embodimet of $R^2$ is hydrogen or lower alkyl (preferably, methyl, ethyl, etc.); the preferred embodiment of $R^3$ is carboxy or diphenyl(lower)alkoxycarbonyl; the preferred embodiment or $R^4$ is hydrogen, acyloxy [preferably lower alkanoyloxy (e.g. acetoxy, etc.) or carbamoyloxy], thiadiazolylthio (more preferably 1,3,4-thiadiazolylthio) which may have lower alkyl (preferably methyl, ethyl, etc.) or tetrazolylthio (more preferably 1H-tetrazolylthio) having lower alkyl (preferably methyl, ethyl, etc.), di(lower)alkylamino(lower)alkyl or lower alkenyl; and the preferred embodiment of $R^5$ is hydrogen or lower alkoxy (preferably methoxy).

The processes for preparing the object compounds (I) and (Ia) are explained in details in the following.

PROCESS 1

The object compound (I) can be prepared by reacting the compound (II) or its reactive derivative at the amino group or a salt thereof with the compound (III) or its reactive derivative at the carboxy group or a salt thereof, and in case that the resulting compound has a protective group on hydroxy in its hydroxyimino group, subjecting the resulting compound to elimination reaction of the said protective group to provide the compound (I) wherein $R^2$ is hydrogen.

Suitable reactive derivative at the amino group of the compound (II) may include Schiff's base type imino or its tautomeric enamine type derivative formed by the reaction of the compound (II) with a carbonyl compound (e.g. aldehyde, ketone, etc.), isocyanate; a silyl derivative formed by the reaction of the compound (II) with a silyl compound [e.g. bis(trimethylsilyl)acetamide, trimethylsilylacetamide, etc.]; a derivative formed by reaction of the compound (II) with phosphorus trichloride or phosgene, and the like.

Suitable salt of the compound (II) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride; an acid azide; a mixed acid anhydride with an acid such as substituted phosphoric acid (e.g., dialkylphosphoric acid, phenylphosphoric acid, diphenylphoshoric acid, dibenzylphosphoric acid, halogenated phosphoric acid, etc.) dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g., benzoic acid, etc.); a symmetrical acid anhydride; an activated amido with imidazole, 4-substituted imidazole, dimethylpyrazole, triazole or tetrazole; an activated ester [e.g., cyanomethyl ester, methoxymethyl ester, dimethyliminomethyl[$(CH_3)_2N^+=CH-$]ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-crosyl thioester, carboxymethyl thioester, pyranyl ester, pyridyl ester, piperidyl ester, 8-quinolyl thioester, or an ester with N,N-dimethylhydroxylamine, 1-hydroxy-2-(1H)pyridone, N-hydroxysuccinimide, N-hydroxyphthalimide or 1-hydroxy-6-chloro-1H-benzotriazole, and the like. These reactive derivatives can be optionally selected from them according to the kind of the compound (III) to be used.

The salts of the compound (III) may be salts with an inorganic base such as an alkali metal salts (e.g., sodium or potassium salt) or an alkaline earth metal salt (e.g., calcium or magnesium salt), a salt with an organic base such as trimethylamine, triethylamine, dicyclohexylamine or the like.

The reaction of the compound (II) with the compound (III) is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence to the reaction. Among these solvents, hydrophilic solvents may be used in a mixture with water.

When the compound (III) is used in free acid form or its salt form in the reaction, the reaction is preferably carried out in the presence of a conventional condensing agent such as carbodiimide compound(e.g.,N,N'-dicyclohexylcarbodiimide, N-cyclohexyl-N'-morpholinoethylcarbodiimide,N-cyclohexyl-N'-(4-diethylaminocyclohexyl)carbodiimide, N,N'-diethylcarbodiimide,N,N'-diisopropylcarbodiimide N-ethyl-N'-(3-dimethylaminopropyl)carbodiimide,etc.),N,N'-carbonylbis(2-methylimidazole), pentamethyleneketone-N-cyclohexylimine, diphenylketene-N-cyclohexylimino, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, N-ethylbenzisoxazolium salt, N-ethyl-5-phenyl-isoxazolium-3'-sulfonate, 1-(p-chlorobenzenesulfonyloxy)-6-chloro-1H-benzotriazole, Vilsmeier reagent [e.g.,(chloromethylene)dimethylammonium chloride, a compound formed by the reaction of dimethylformamide with phosphorus oxychloride, etc.], or the like.

The reaction may be also carried out in the presence of an inorganic or an organic base such as an alkali metal bicarbonate, alkali metal carbonate, tri(lower)alkylamine, pyridine, N-(lower)alkylmorphorine, N,N-di(lower)alkylbenzylamine, N,N-di(lower)alkylaniline, or the like. When the base or the condensing agent is in liquid, it can be used also as a solvent. The reaction temperature is not critical, and the reaction is usually carried out under cooling or at ambient temperature.

In the present reaction, even when the compound (III), wherein $R^{2'}$ is a hydroxy protective group, is used as a starting compound, occasionally the object compound (I), wherein $R^2$ is hydrogen, can be isolated from the reaction mixture depending on a kind of the hydroxy protective group, reaction conditions and the like.

In case that the resulting compound obtained by this process has a hydroxy protective group on hydroxy in its hydroxyimino group, the said protective group is eliminated by a conventional method (e.g. hydrolysis, etc.) to provide the compound (I) wherein $R^2$ is hydrogen. That is, for example, the elimination of the said protective group is usually conducted by a method using acid (e.g. hydrochloric acid, hydrobromic acid, sulfuric acid, trifluoroacetic acid, etc.) or a base, for example, an inorganic base such as an alkali metal hydroxide (e.g., sodium hydroxide, potassium hydroxide etc.), an alkali metal bicarbonate (e.g., sodium bicarbonate, potassium bicarbonate etc.) or an alkali metal carbonate (e.g., sodium carbonate, potassium carbonate etc.), an organic base such as an alkali metal alkoxide (e.g., sodium methoxide, sodium ethoxide etc.), a trialkylamine (e.g., trimethylamine, triethylamine etc.), triethanolamine, N,N-dimethylaniline, N,N-dimethylbenzylamine, N-methylmorpholine or pyridine; and an elimination reaction using silica gel, basic or acidic alumina, basic or acidic ion exchange resin, thiourea, trifluoroacetic acid/anisole, copper/dimethylformamide, zinc/dimethylformamide, zinc/acetic acid, zinc/formic acid, trifluoroacetic acid/zinc etc. The present elimination reaction is usually carried out in water, hydrophilic solvent or a mixture thereof. The reaction temperature is not critical and the reaction is preferably carried out at ambient temperature, or under cooling.

And, the protected carboxy group or salts in the compound (II) may be transformed into the corresponding free carboxy group in the course of the reaction and/or in post-treatment according to the reaction conditions.

The mode of reactions occured in the course of the acylation reaction and/or in post-treatment as mentioned above (i.e. transformation of protected carboxy group into the free carboxy group) is to be understood to be included within the scope of the present invention.

In this process, there may occur partially or nearly complete isomerization between syn and anti geometry of the compound (III) in the course of the activation process thereof or the reaction with the compound (II) (i.e. acylation), depending on surrounding such as reaction conditions or the like. Generally, such isomerization tends to be equilibrated toward the more stable anti-geometry. Under such chemical behaviors of the compound (III), in case of preparing the syn isomer of the object compound (I) selectively and preparing it in good yield, it is to be noted that it is essential to use syn isomer of the compound (III) as a starting compound and to select the reaction conditions suitable for producing the syn isomer selectively and in good yield. For example, for this purpose, the acylation reaction in this process is more preferably conducted by reacting the compounds (II) and (III) in the presence of a condensing agent such as Vilsmeier reagent, etc. and in a reaction condition such as around neutral.

PROCESS 2

The object compound (Ia) or a salt thereof can be prepared by subjecting the compound (IV) or a salt thereof to elimination reaction of the carboxy protective group.

Suitable salt of the compound (IV) can be referred to the acid addition salt exemplified for the compound (II).

In the present elimination reaction, all conventional methods used in the elimination reaction of the carboxy protective group, for example, hydrolysis, reduction, etc. are applicable. When the carboxy protective group is an ester, it can be eliminated by hydrolysis. The hydrolysis is preferably carried out in the presence of a base or an acid. Suitable base may include an inorganic base and an organic base as aforementioned in process 1.

Suitable acid may include an organic acid (e.g., formic acid, acetic acid, trifluoroacetic acid, propionic acid, etc.) and an inorganic acid (e.g., hydrochloric acid, hydrobromic acid, sulfuric acid, etc.). Trifluoroacetic acid may be used in the presence of anisole.

The present hydrolysis is usually carried out in an organic solvent, water or a mixed solvent thereof.

The reaction temperature is not critical, and it may be suitably selected in accordance with the kind of the protective group of the carboxy and the elimination method.

The reduction is carried out in a similar manner to that of process (D) as mentioned below in the part of preparations of the starting compound (III).

Processes for preparing the starting compund (III) are explained as follows.

PROCESS (A): (IV)→(V) and (X)→(XI)

The compounds (V) and (XI) can be prepared by alkylating the compounds (IV) and (X), respectively.

The alkylating agent to be used in these alkylation reactions may include di(lower)alkyl sulfate (e.g., dimethyl sulfate, diethyl sulfate, etc.), diazo(lower)alkane (e.g., diazomethane, diazoethane, etc.), lower alkyl halide (e.g., methyl iodide, ethyl iodide, etc.), lower alkyl sulfonate (e.g., methyl p-toluenesulfonate, etc.), and the like.

The reaction by using di(lower)alkyl sulfate, lower alkyl halide or lower alkyl sulfonate is usually carried out in a solvent such as water, acetone, ethanol, ether, ethyl acetate, dimethylformamide or any other solvent which does not adversely influence to the reaction, and is preferably carried out in the presence of a base such as aforementioned inorganic or organic base. The reaction temperature is not critical and the reaction is usually carried out under cooling to heating around boiling point of the solvent.

The reaction by using diazoalkane is usually carried out in a solvent such as ether, tetrahydrofuran or the like. The reaction temperature is not critical and the reaction is usually carried out under cooling or at ambient temperature.

PROCESS (B): (B)+(VI)→(VII)

The compound (VII) can be prepared by reacting the compound (V) with the compound (VI).

The present reaction is usually carried out in a solvent such as an alcohol (e.g., methanol, ethanol, etc.), chloroform, water or any other solvent which does not adversely affect the reaction. The reaction temperature is not critical and the reaction is usually carried out at ambient temperature or under warming.

PROCESS (C): (VII)→(VIII)

The compound (VIII) can be prepared by reacting the compound (VII) with a sulfurizating agent.

Suitable sulfurizating agent may include conventional ones, which can sulfurize an active methylene group, for example, sulfur, ammonium sulfide, sulfur dihalide (e.g., sulfur dichloride, sulfur dibromide, etc.), thionyl halide (e.g., thionyl chloride, thionyl bromide, etc.) or the like.

The reaction can be carried out with or without solvent, and as a solvent, there is used benzene, methylene chloride or any other solvent which does not adversely affect the reaction. The reaction temperature is not critical and the reaction is usually carried out at ambient temperature, under warming or heating.

PROCESS (D): (VIII)→(III$_a$), (XI)→(III$_b$) and (XII)→(XIII)

The compound (III$_a$), (III$_b$) and (XIII) can be prepared by subjecting the compound (VIII), (XI) and (XII) to elimination reaction of their carboxy protective group, respectively.

In the present elimination reaction, all conventional methods, for example, hydrolysis, reduction, etc. can be applicable.

When the protected carboxy group is an ester, the protective group can be eliminated preferably by hydrolysis. Hydrolysis is preferably carried out in the presence of a base or an acid. Suitable base may include an inorganic base and an organic base such as an alkali metal (e.g., sodium, potassium, etc.), an alkaline earth metal (e.g., magnesium, calcium, etc.), the hydroxide or carbonate or bicarbonate thereof, trialkylamine (e.g., trimethylamine, triethylamine, etc.), picoline, 1,5-diazabicyclo[4,3,0]none-5-ene, 1,4-diazabicyclo[2,2,-2]octane, 1,8-diazabicyclo[5,4,0]undecene-7, or the like. Suitable acid may include an organic acid (e.g., formic acid, acetic acid, propionic acid, trifluoroacetic acid, etc.) and an inorganic acid (e.g., hydrochloric acid, hydrobromic acid, sulfuric acid, etc.).

The reaction is usually carried out in a solvent such as water, an alcohol (e.g., methanol, ethanol, etc.), a mixture thereof or any other solvent which does not adversely influence to the reaction. A liquid base or acid can be also used as the solvent. The reaction temperature is not critical and the reaction is usually carried out under cooling to warming.

Reduction can be applied preferably for elimination of the protective group such as 2-iodoethyl, 2,2,2-trichloroethyl, or the like. The reduction method applicable for the elimination reaction may include, for example, reduction by using a combination of a metal (e.g., zinc, zinc amalgam, etc.) or a salt of chrome compound (e.g., chromous chloride, chromous acetate, etc.) and an organic or inorganic acid (e.g., acetic acid, propionic acid, hydrochloric acid etc.); and conventional catalytic reduction in the presence of a conventional metallic catalyst.

PROCESS (E): (IX)→(X)

The compound (X) can be prepared by subjecting the compound (IX) to nitrosation.

The nitrosating agent to be used in the reaction is conventional ones, which can react with an active methylene compound to produce C-nitroso compound, including for example, nitrous acid or its's salt such as alkali metal nitrite (e.g., sodium nitrite, etc.) or it's ester such as lower alkyl nitrite (e.g., tert-butyl nitrite, isopentyl nitrite, etc.), and the like.

The reaction, when a salt of nitrous acid is used as the nitrosating agent, is usually carried out in the presence of an inorganic or organic acid such as hydrochloric acid, sulfuric acid, acetic acid or the like. On the contrary, when an ester of nitrous acid is used as the nitrosating agent, the reaction is preferably carried out in the presence of a rather strong base such as an alkali metal alkoxide (e.g. sodium methoxide, sodium ethoxide, potassium tert-butoxide, etc.) and the like.

The present reaction is usually carried out in a solvent such as water, acetic acid, alcohol (e.g., ethanol, methanol, etc.), ether, tetrahydrofuran or any other solvent which does not adversely influence to the reaction. The reaction temperature is not critical and the reaction is usually carried out under cooling or at ambient temperature.

PROCESS (F): (IX)→(XII)

The compound (XII) can be prepared by oxidizing the compound (IX) with an oxidizing agent.

Suitable oxidizing agent is conventional ones, which can oxidize an active methylene group into carbonyl group, including, for example, selenium dioxide, manganous acetate and potassium permanganate or the like.

The reaction is usually carried out in a solvent which does not adversely influence to the reaction, for example, water, dioxane, pyridine, tetrahydrofuran, and the like. The reaction temperature is not critical and the reaction is preferably carried out under warming to heating.

PROCESS (G): (X)→(XIII)

The compound (XIII) can be prepared by hydrolyzing the compound (X).

The hydrolyis is conventionally carried out, for example, in the presence of alkali metal bisulfite (e.g., sodium bisulfite, etc.) titanium trichloride, hydrohalogenic acid (e.g., hydrochloric acid hydrobromic acid, etc.), formic acid, nitrous acid or the like, and preferably hydrohalogenic acid may be used in the presence of an aldehyde such as formaldehyde, etc.

The reaction is usually carried out in an aqueous solvent such as water, aqueous alcohol (e.g., methanol ethanol, etc.), aqueous acetic acid or any other aqueous solvent which does not adversely influence to the reaction. The reaction temperature is not critical and the reaction is usually carried out at ambient temperature, under warming or heating.

PROCESS (H): (XIII)+(XIV)→(III$_b$)

The compound (III$_b$) can be prepared by reacting the compound (XIII) with the compound (XIV) or a salt thereof.

Suitable salt of the compound (XIV) may include an inorganic acid salt (e.g., hydrochloride, hydrobromide, sulfate, etc.), an organic acid salt (e.g., acetate, maleate, p-toluenesulfonate, etc.) and the like.

The reaction is usually carried out in a solvent such as water, an alcohol (e.g., methanol, ethanol, etc.), a mixture thereof or any other solvent which does not adversely influence to the reaction.

The reaction is preferably carried out in the presence of a base, for example, an inorganic base such as alkali metal (e.g., sodium, potassium, etc.), alkaline earth metal (e.g., magnesium, calcium etc.), the hydroxide or carbonate or bicarbonate thereof or the like, and an organic base such as alkali metal alkoxide (e.g., sodium methoxide, sodium ethoxide, etc.), trialkylamine (e.g. trimethylamine, triethylamine, etc.), N,N-dialkylamine (e.g., N,N-dimethylaniline, etc.), N,N-dialkylbenzylamine (e.g., N,N-dimethylbenzylamine, etc.), pyridine or the like.

The reaction temperature is not critical and the reaction is usually carried out under cooling to heating.

In this process, there may occasionally be given a mixture of syn and anti isomers of the compound ($III_b$) depending on the reaction conditions etc. to be used. Each of said syn and anti isomers can be separated and isolated from such mixture according to conventional separation and isolation procedures, for example, esterification of said mixture, separation of the esters into each of syn and anti isomers by, for example, chromatographical fractionation and then recovery of each of the corresponding carboxylic acid from each of the separated syn and anti isomeric esters by hydrolyzing the said ester functions, respectively.

PROCESS (I): (XIII)→($III_c$)

The compound ($III_c$) can be prepared by reacting the compound (XIII) with hydroxylamine or a salt thereof.

Suitable salt of hydroxylamine can be referred to the ones exemplified for the compound (XIV).

The reaction is preferably conducted substantially in the similar manner as that exemplified in the Process (H): (XIII)+(XIV)→($III_b$). The present reaction may preferably be carried out in the presence of alkaline earth metal hydroxide (e.g., magnesium hydroxide, calcium hydroxide, etc.).

PROCESS (J): ($III_c$)→($III_d$)

The compound ($III_d$) can be prepared by subjecting the compound ($III_c$) to introduction reaction of a protective group for hydroxy.

Suitable introducing agent may include an acylating agent which includes an aliphatic aromatic or heterocyclic carboxylic acid, and the corresponding sulfonic acid, formic acid ester, isocyanic acid ester and carbamic acid, and the corresponding thio acid thereof, and the reactive derivative of the above acids. Suitable reactive derivative of the above acids may include the same ones as illustrated in the explanation of "reactive derivative at the carboxy group of the compound (III)".

Examples of the protective group (e.g. acyl group) to be introduced into the hydroxyimino group in the compound ($III_c$) may be referred to the same one (e.g., acyl group) as illustrated in the explanation of the protective group moiety (e.g., acyl moiety) for the term "acylamino".

The reaction is carried out substantially in the same manner as illustrated in the reaction of the compound (II) or its reactive derivative at the amino group or a salt thereof with the compound (III) or its reactive derivative at the carboxy group.

In the aforementioned reactions and/or the post-treating of the reactions of the present invention, the aforementioned syn or anti isomer may occasionally transformed into the other geometrical isomer and such cases are to be also included in the scope of the present invention.

In case that the object compound (I) is obtained in a form of the free acid at 4 position and/or in case that the object compound (I) has free amino group, it may be transformed into its pharmaceutically acceptable salt as aforementioned by a conventional method.

The object compound (I) of the present invention exhibits high antimicrobial activity and inhibits the growth of a number of microorganisms including pathogenic Gram-positive and Gram-negative bacteria. And, it is to be noted that, among the object compounds, particularly the syn isomer thereof is characterized by having higher antimicrobial activity.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid for such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases causes by a number of pathogenic bacteria. In general amounts between 1 mg. and about 1000 mg. or even more may be administered per day.

Now, in order to show the utility of the object compounds (I), test data on anti-microbial activity of some representative compounds of the present invention are shown below.

TEST COMPOUNDS (1) 7-[2-Methoxyimino-2-(1,2,3-thiadiazol-4-yl)acetamido]-3-(1-methyl-1H-tetrazol-5-yl)thiomethyl-3-cephem-4-carboxylic acid (syn isomer)

(2) 7-[2-Methoxyimino-2-(1,2,3-thiadiazol-4-yl)acetamido]-3-(1-methyl-1H-tetrazol-5-yl)thiomethyl-3-cephem-4-carboxylic acid (anti isomer)

(3) 7-[2-Hydroxyimino-2-(1,2,5-thiadiazol-3-yl)acetamido]-3-(1-methyl-1H-tetrazol-5-yl)thiomethyl-3-cephem-4-carboxylic acid (syn isomer)

(4) 7-[2-Hydroxyimino-2-(isothiazol-4-yl)acetamido]-3-(1-methyl-1H-tetrazol-5-yl)thiomethyl-3-cephem-4-carboxylic acid (syn isomer)

TEST METHOD

In vitro antibacterial activity was determined by the two-fold agar-plate dilution method as described below.

One loopful of an overnight culture of each test strain in Trypticase-soy broth ($10^8$ viable cells per ml.) was streaked on heart infusion agar (III-agar) containing graded concentrations of antibiotics, and the minimal inhibitory concentration (NIC) was expressed in terms of μg/ml. after incubation at 37° C. for 20 hours.

| Test Bacteria | Test results MIC (μg/mL.) Test Compounds | | | |
|---|---|---|---|---|
| | (1) | (2) | (3) | (4) |
| *Staph. aureus* 209P JC-1 | 3.13 | 12.5 | 0.78 | 0.39 |
| *E. coli* NIHJ JC-2 | 0.78 | 25 | 3.13 | 1.56 |
| *Sh. flexneri* 2a | 1.56 | 12.5 | 0.39 | 0.39 |
| *Sal. enteritidis* | 0.2 | 6.25 | 1.56 | 0.78 |

The following examples are given for the purpose of illustrating the present invention:

EXAMPLE 1

(a) Preparation of the starting compound (1) Pulverized potassium carbonate (160 g.) was added to a solution of ethyl 2-hydroxyiminoacetoacetate (a mixture of syn and anti isomers) (152 g.) in acetone (500 ml.). Dimethyl sulfate (130 g.) was dropwise added thereto with stirring over 1 hour at 45° to 50° C. and the mixture was stirred for 2 hours. An insoluble material was filtered off and the filtrate was concentrated under reduced pressure. The filtered insoluble material was dissolved in water (500 ml.) and this solution was added to the residue. The mixture was extracted twice with ethyl acetate (300 ml.). The extract was washed twice with water (200 ml.) and with a saturated sodium chloride aqueous solution (200 ml.) and dried over magnesium sulfate. The solvent was distilled off under reduced pressure and the residue was distilled under reduced pressure to give colorless oil of ethyl 2-methoxyiminoacetoacetate (a mixture of syn and anti isomers) (145.3 g.), bp 55° to 64° C./0.5 mm Hg.

I.R. spectrum (Film): 1745, 1695, 1600 cm$^{-1}$.

N.M.R. spectrum (CDCl$_3$, δ), ppm: 4.33 (4H, q, J=8 Hz), 4.08 (3H, s), 3.95 (3H, s), 2.40 (3H, s), 1.63 (3H, s), 1.33 (6H, t, J=8 Hz).

(2) A solution of ethyl 2-methoxyiminoacetoacetate (a mixture of syn and anti isomers) (34.6 g.) and t-butoxycarbonylhydrazine (26.4 g.) in ethanol (200 ml.) was stirred for 7.5 hours at ambient temperature and allowed to stand overnight to precipitate crystals. The crystals were collected by filtration, washed with ethanol and dried to give ethyl 2-methoxyimino-3-t-butoxycarbonylhydrazonobutyrate (a mixture of syn and anti isomers) (41.7 g.), mp 144° to 145° C.

I.R. spectrum (Nujol): 3200, 1750, 1705, 1600, 1520 cm$^{-1}$.

N.M.R. spectrum (CDCl$_3$, δ) ppm: 8.52 (1H, broad s), 4.35 (2H, q, J=7 Hz), 4.10 (3H, s), 2.00 (3H, s), 1.50 (9H, s), 1.33 (3H, t, J=7 Hz).

(3) A mixture of ethyl 2-methoxyimino-3-t-butoxycarbonylhydrazonobutyrate (a mixture of syn and anti isomers) (28.7 g.) and thionyl chloride (30 ml.) was warmed with stirring on a water bath of 50° C. for 3 minutes and then stirred for 5 minutes at ambient temperature to give black solution. To the reaction mixture was added ethyl acetate (200 ml.) and the mixture was poured into ice-water (300 ml.). The ethyl acetate layer was separated, washed in turn with water, with a saturated aqueous solution of sodium bicarbonate and with a saturated aqueous solution of sodium chloride. After drying over magnesium sulfate, the ethyl acetate solution was treated with activated charcoal and concentrated to give black oil. The oil was purified by column chromatography on silica gel using a mixture of benzene and ethyl acetate (19:1) as an eluent to give ethyl 2-methoxyimino-2-(1,2,3-thiadiazol-4-yl)acetate (anti isomer) (4 g.).

I.R. spectrum (Film): 1730, 1590 cm$^{-1}$.

N.M.R. spectrum (CDCl$_3$, δ) ppm: 9.38 (1H, s), 4.47 (2H, q, J=7 Hz), 4.20 (3H, s), 1.40 (3H, t, J=7 Hz).

(4) Sulfur dichloride (15.9 ml.) was added with stirring at ambient temperature to a solution of ethyl 2-methoxyimino-3-t-butoxycarbonylhydrazonobutyrate (a mixture of syn and anti isomers) (14.36 g.) in methylene chloride (150 ml.), and the mixture was stirred for 1 hour at ambient temperature. To the reaction mixture was added ice-water (300 ml.), and the methylene chloride layer was washed with water, with a saturated aqueous solution of sodium bicarbonate and with a saturated aqueous solution of sodium chloride and dried over magnesium sulfate. The solvent was distilled off to give an oil. The oil was purified by column chromatography on silica gel using a mixture of benzene and n-hexane (19:1) as an eluent to firstly give ethyl 2-methoxyimino-2-(1,2,3-thiadiazol-4-yl)acetate (syn isomer) (1.8 g.), mp 77° to 79° C.

I.R. spectrum (Nujol): 1720, 1595 cm$^{-1}$.

N.M.R. spectrum (CDCl$_3$, δ) ppm: 8.92 (1H, s), 4.46 (2H, q, J=7 Hz), 4.06 (3H, s), 1.38 (3H, t, J=7 Hz).

From subsequent fractions, ethyl 2-methoxyimino-2-(1,2,3-thiadiazol-4-yl)acetate (anti isomer) (0.7 g.) was obtained as an oil.

I.R. spectrum (Film): 1730, 1590 cm$^{-1}$.

N.M.R. spectrum (CDCl$_3$, δ) ppm: 9.38 (1H, s), 4.47 (2H, q, J=7 Hz), 4.20 (3H, s), 1.40 (3H, t, J=7 Hz).

(5) A solution of sodium hydroxide (0.47 g.) in water (10 ml.) was added to a solution of ethyl 2-methoxyimino-2-(1,2,3-thiadiazol-4-yl)acetate (anti isomer) (2.1 g.) in methanol (20 ml.) and the resulting mixture was stirred for 6 hours at ambient temperature. Methanol was removed from the reaction mixture and to the residue was added water. The resulting mixture was washed with ether, adjusted to pH 1 with 10% hydrochloric acid and extracted twice with ether (50 ml.). The extract was washed with a saturated aqueous solution of sodium chloride and dried over magnesium sulfate. The solvent was distilled off to give oil of 2-methoxyimino-2-(1,2,3-thiadiazol-4-yl)acetic acid (anti isomer) (1.3 g.).

I.R. spectrum (Film): 2700–2200, 1715, 1600 cm$^{-1}$.

(b) Preparation of the object compound

A mixture of dimethylformamide (0.56 g.) and phosphorus oxychloride (1.17 g.) was warmed for 1 hour at 40° C. After cooling, methylene chloride (10 ml.) was added thereto and distilled off. The residue was suspended in dry ethyl acetate (10 ml.). To the suspension was added a solution of 2-methoxyimino-2-(1,2,3-thiadiazol-4-yl)acetic acid (anti isomer) (1.3 g.) in dry ethyl acetate (10 ml.) with stirring and ice-cooling, and the resulting mixture was stirred for 30 minutes at the same temperature. On the other hand, 7-amino-3-(1,3,4-thiadiazol-2-yl)thiomethyl-3-cephem-4-carboxylic acid (2.3 g.) was dissolved in a solution of trimethylsilylacetamide (5.9 g.) in dry ethyl acetate (40 ml.). To the solution was added the above-obtained ethyl acetate solution with stirring at −20° C., and the mixture was stirred for 1.5 hours at −10° to −20° C. After water (60 ml.) was added to the reaction mixture at −20° C., precipitates were collected by filtration and washed with acetone. The filtrate and the washings were combined and the organic layer was separated. The aqueous layer was extracted with ethyl acetate. The extract was combined with the organic layer obtained above and the mixture was treated with activated charcoal. The charcoal was filtered off and the filtrate was adjusted to ph 7 with an aqueous solution of sodium bicarbonate after adding water (100 ml.). The aqueous layer was separated and ethyl acetate (100 ml.) was added thereto. The mixture was adjusted to pH 2 with 10% hydrochloric acid and extracted with ethyl acetate. The aqueous layer was further extracted with ethyl acetate (50 ml.). The ethyl acetate extracts were combined, washed with a saturated aqueous solution of sodium chloride and dried over magnesium sulfate. After the solvent was distilled off, ether was added to the residue to give powder. The powder was collected by filtration and dried to give 7-[2-methoxyimino-2-(1,2,3-thiadiazol-4-yl)acetamido]-3-(1,3,4-thiadiazol-2-yl)thiomethyl-3-cephem-4-carboxylic acid (anti isomer) (0.6 g.).

I.R. spectrum (Nujol): 3150, 1760, 1705, 1660, 1590, 1530 cm$^{-1}$.

N.M.R. spectrum (d$_6$-DMSO, δ) ppm: 9.68 (1H, s), 9.58 (1H, d, J=8 Hz), 9.51 (1H, s) 5.84 (1H, dd, J=5,8 Hz), 5.20 (1H, d, J=5 Hz), 4.45 (2H, AB$_q$, J=13 Hz), 4.07 (3H, s), 3.72 (2H, AB$_q$, J=17 Hz).

EXAMPLE 2

(a) Preparation of the starting compound (1) A solution of ethyl 2-methoxyiminoacetoacetate (a mixture of syn and anti isomer) (226.6 g.) and acetohydrazide (78.5 g.) in ethanol (500 ml.) was stirred for 1.5 hours at ambient temperature. Precipitates were collected by filtration, washed with ethanol and ether and dried to give ethyl 2-methoxyimino-3-acetylhydrazonobutyrate (a mixture of syn and anti isomers) (155.7 g.), mp 190° to 191.5° C.

I.R. spectrum (Nujol): 3150, 1725, 1660, 1600, 1585 cm$^{-1}$.

N.M.R. spectrum (CDCl$_3$, δ) ppm: 9.82 (1H, s), 4.32 (2H, q, J=7 Hz), 3.97 (3H, s), 2.20 (3H, s), 2.10 (3H, s), 1.35 (3H, t, J=7 Hz).

(2) A mixture of ethyl 2-methoxyimino-3-acetylhydrazonobutyrate (a mixture of syn and anti isomers) (22.9 g.) and thionyl chloride (51 g.) was warmed at 45° C. with stirring on water bath for 10 minutes. To the reaction mixture was added ethyl acetate (200 ml.) and the resulting mixture was poured into ice-water (300 ml.). The ethyl acetate layer was separated, in turn washed with water, with a saturated aqueous solution of sodium bicarbonate and with a saturated aqueous solution of sodium chloride and then dried over magnesium sulfate. After treating with activated charcoal, the solvent was distilled off to give black oil. The oil was purified by column chromatography on silica gel using benzene as an eluent to firstly give ethyl 2-methoxyimino-2-(1,2,3-thiadiazol-4-yl)acetate (syn isomer) (2 g.), mp 77° to 79° C.

I.R. spectrum (Nujol): 1720, 1595 cm$^{-1}$.

N.M.R. spectrum (CDCl$_3$, δ) ppm: 8.92 (1H, s), 4.46 (2H, q, J=7 Hz), 4.06 (3H, s), 1.38 (3H, t, J=7 Hz).

From subsequent fractions, ethyl 2-methoxyimino-2-(1,2,3-thiadiazol-4-yl) acetate (anti isomer) (6.4 g.) was obtained as an oil.

I.R. spectrum (Film): 1730, 1590 cm$^{-1}$.

N.M.R. spectrum (CDCl$_3$, δ) ppm: 9.38 (1H, s), 4.47 (2H, q, J=7 Hz), 4.20 (3H, s), 1.40 (3H, t, J=7 Hz).

(3) 1N Aqueous solution of sodium hydroxide (6.7 ml.) was added to a solution of ethyl 2-methoxyimino-2-(1,2,3-thiadiazol-4-yl)acetate (syn isomer) (1.2 g.) in methanol (10 ml.) and the mixture was stirred for 1.5 hours at ambient temperature. Methanol was distilled off from the reaction mixture and water was added to the residue. The mixture was washed with ether, adjusted to pH 1 with 10% hydrochloric acid and extracted with ethyl acetate. The extract was washed with a saturated aqueous solution of sodium chloride and dried over magnesium sulfate. The solvent was distilled off to give prisms of 2-methoxyimino-2-(1,2,3-thiadiazol-4-yl)acetic acid (syn isomer) (0.7 g.), mp 110° to 113° C.

I.R. spectrum (Nujol): 2750–2150, 1730, 1595 cm$^{-1}$.

N.M.R. spectrum (d$_6$-DMSO, δ) ppm: 9.47 (1H, s), 4.01 (3H, s).

(b) Preparation of the object compound

2-Methoxyimino-2-(1,2,3-thiadiazol-4-yl)-acetic acid (syn isomer) (0.6 g.) and 7-amino-3-(1,3,4-thiadiazol-2-yl)thiomethyl-3-cephem-4-carboxylic acid (1.1 g.) were reacted according to similar manners to those of Examples 12 and 15 to give 7-[2-methoxyimino-2-(1,2,3-thiadiazol-4-yl)acetamido]-3-(1,3,4-thiadiazol-2-yl)thiomethyl-3-cephem-4-carboxylic acid (syn isomer) (0.7 g.), mp 90° to 98° C. (dec.).

I.R. spectrum (Nujol): 3250, 1780, 1725, 1680, 1530 cm$^{-1}$.

N.M.R. spectrum (d$_6$-DMSO, δ) ppm: 9.82 (1H, d, J=8 Hz), 9.51 (1H, s), 9.37 (1H, s), 5.88 (1H, dd, J=5,8 Hz), 5.20 (1H, d, J=5 Hz), 4.44 (2H, AB$_q$, J=13 Hz), 3.99 (3H, s), 3.72 (2H, AB$_q$, J=17 Hz).

EXAMPLE 3

(a) Preparation of the starting compound (1) A sodium ethoxide solution which was prepared from sodium (230 mg.) and absolute ethanol (5 ml.) was dropwise added at 0° to 5° C. to a solution of ethyl 2-(5-methyl-1,3,4-thiadiazol-2-yl)acetate (1.86 g.) and isopentyl nitrite (3 ml.) in absolute ethanol (25 ml.). The resulting mixture was stirred for 3 hours at the same temperature and for 1 hour at ambient temperature. The reaction mixture was acidified with 10% hydrochloric acid to precipitate crystals. After ethanol was distilled off under reduced pressure at 30° C., water (30 ml.) was added to the residue, after which the mixture was extracted three times with ethyl acetate (30 ml.). The extracts were washed with water and dried over sodium sulfate. The solvent was distilled off under reduced pressure to give crystals of ethyl 2-hydroxyimino-2-(5-methyl-1,3,4-thiadiazol-2-yl)acetate (a mixture of syn and anti isomers) (1.50 g.). The crystals were recrystallized from ethyl acetate to give pure crystals, mp 181° to 184° C. (dec.).

I.R. spectrum (Nujol): 3120, 2800–2100, 1742 cm$^{-1}$.

N.M.R. spectrum (d$_6$-DMSO, δ) ppm: 4.37 (2H, q, J=7 Hz), 2.80 (3H, s), 1.30 (3H, t, J=7 Hz).

(2) Potassium carbonate (2.85 g.) and dimethyl sulfate (2.2 g.) were added to a suspension of ethyl 2-hydroxyimino-2-(5-methyl-1,3,4-thiadiazol-2-yl)acetate (a mixture of syn and anti isomers) (3.7 g.) in ethyl acetate (60 ml.), and the resulting mixture was stirred for 6 hours at 40° to 45° C. The reaction mixture was washed with water (50 ml.) and dried over magnesium sulfate. The solvent was distilled off to give oil (2.5 g.). The oil was purified by column chromatography on silica gel using a mixture of benzene and ethyl acetate (9:1) as an eluent to firstly give ethyl 2-methoxyimino-2-(5-methyl-1,3,4-thiadiazol-2-yl)acetate (syn isomer) (0.3 g.), mp 104° to 106° C.

I.R. spectrum (Nujol): 1735, 1590 cm$^{-1}$.

N.M.R. spectrum (CDCl$_3$, δ) ppm: 4.42 (2H, q, J=7 Hz), 4.03 (3H, s), 2.77 (3H, s), 1.37 (3H, t, J=7 Hz).

From subsequent fractions, ethyl 2-methoxyimino-2-(5-methyl-1,3,4-thiadiazol-2-yl)acetate (anti isomer) (1.3 g.), mp 79° to 81° C., was obtained.

I.R. spectrum (Nujol): 1735, 1700, 1600 cm$^{-1}$.

N.M.R. spectrum (CDCl$_3$, δ) ppm 4.42 (2H, q, J=7 Hz), 4.17 (3H, s), 2.82 (3H, s), 1.37 (3H, t, J=7 Hz).

(3) Ethyl 2-methoxyimino-2-(5-methyl-1,3,4-thiadiazol-2-yl)-acetate (syn isomer) (0.4 g.) and 1N aqueous solution of sodium hydroxide (2.1 ml.) were treated according to a similar manner to that of Example 1(a)(5) to give 2-methoxyimino-2-(5-methyl-1,3,4-thiadiazol-2-yl)acetic acid (syn isomer) (0.25 g.), mp 168° to 171° C. (dec.).

I.R. spectrum (Nujol): 2750–2150, 1725, 1600 cm$^{-1}$.

N.M.R. spectrum (d$_6$-DMSO, δ) ppm: 4.00 (3H, s), 2.74 (3H, s)

(b) Preparation of the object compound

2-Methoxyimino-2-(5-methyl-1,3,4-thiadiazol-2-yl)acetic acid (syn isomer) (0.21 g.) and 7-amino-3-(1,3,4-thiadiazol-2-yl)-thiomethyl-3-cephem-4-carboxylic acid (0.41 g.) were reacted according to similar manners to those of Examples 12 and 15 to give 7-[2-methoxyimino-2-(5-methyl-1,3,4-thiadiazol-2-yl)acetamido]-3-(1,3,4-thiadiazol-2-yl)thiomethyl-3-cephem-4-carboxyic acid (syn isomer) (0.23 g.), mp 175° to 178° C. (dec.).

I.R. spectrum (Nujol): 3250, 1785, 1700, 1665, 1620, 1590, 1550 cm$^{-1}$.

N.M.R. spectrum (d$_6$-DMSO, δ) ppm: 9.83 (1H, d, J=8 Hz), 9.57 (1H, s), 5.87 (1H, dd, J=5,8 Hz), 5.18 (1H, d, J=5 Hz), 4.43 (2H, AB$_q$, J=13 Hz), 4.00 (3H, s), 3.70 (2H, AB$_q$, J=17 Hz), 2.77 (3H, s).

EXAMPLE 4

(a) Preparation of the starting compound

Ethyl 2-methoxyimino-2-(5-methyl-1,3,4-thiadiazol-2-yl)acetate (anti isomer) (1.2 g.) and 1N aqueous solution of sodium hydroxide (10.5 ml.) were treated according to a similar manner to that of Example 1(a)(5) to give 2-methoxyimino-2-(5-methyl-1,3,4-thiadiazol-2-yl)acetic acid (anti isomer) (1.06 g.), mp 173° to 174° C. (dec.).

I.R. spectrum (Nujol): 2700–2150, 1660, 1540 cm$^{-1}$.

N.M.R. spectrum (d$_6$-DMSO, δ) ppm: 4.12 (3H, s), 2.79 (3H, s).

(b) Preparation of the object compound

2-Methoxyimino-2-(5-methyl-1,3,4-thiadiazol-2-yl)acetic acid (anti isomer) (0.99 g.) and 7-amino-3-(1,3,4-thiadiazol-2-yl)thiomethyl-3-cephem-4-carboxylic acid (1.62 g.) were reacted according to a similar manner to that of Example 1(b) to give 7-[2-methoxyimino-2-(5-methyl-1,3,4-thiadiazol-2-yl)acetamido]-3-(1,3,4-thiadiazol-2-yl)thiomethyl-3-cephem-4-carboxylic acid (anti isomer) (1.25 g.), mp 110° to 115° C. (dec.).

I.R. spectrum (Nujol): 3200, 1780, 1730, 1680, 1630, 1530 cm$^{-1}$.

N.M.R. spectrum (d$_6$-DMSO, δ) ppm: 9.74 (1H, d, J=8 Hz), 9.52 (1H, s), 5.86 (3H, dd, J=5,8 Hz), 5.20 (1H, d, J=5 Hz), 4.45 (2H, AB$_q$, J=13 Hz), 4.16 (3H, s), 3.72 (2H, AB$_q$, J=17 Hz), 2.90 (3H, s).

EXAMPLE 5

(a)

(1) Ethyl 2-(1,2,5-thiadiazol-3-yl)acetate (9.5 g.) and isopentyl nitrite (10 ml.) were reacted according to a similar manner to that of Example 3(a)(1) to give ethyl 2-hydroxyimino-2-(1,2,5-thiadiazol-3-yl)acetate (a mixture of syn and anti isomers) (10.5 g.), mp 60° to 66° C.

I.R. spectrum (Nujol): 3150, 1710 cm$^{-1}$.

N.M.R. spectrum (d$_6$-DMSO, δ) ppm: 9.27 (1H, s), 4.33 (2H, q, J=7 Hz), 1.30 (3H, t, J=7 Hz).

(2) Ethyl 2-hydroxyimino-2-(1,2,5-thiadiazol-3-yl)acetate (a mixture of syn and anti isomers) (10.4 g.) and dimethyl sulfate (6.5 g.) were reacted according to a similar manner to that of Example 3(a)(2) and the oil obtained was purified by column chromatography on silica gel using benzene as an eluent to firstly give oil of ethyl 2-methoxyimino-2-(1,2,5-thiadiazol-3-yl)acetate (syn isomer) (0.5 g.).

I.R. spectrum (Film): 1735, 1592 cm$^{-1}$.

N.M.R. spectrum (CDCl$_3$, δ) ppm: 8.96 (1H, s), 4.50 (2H, q, J=7 Hz), 4.13 (3H, s), 1.42 (3H, t, J=7 Hz), From subsequent fractions, ethyl 2-methoxyimino-2-(1,2,5-thiadiazol-3-yl)acetate (anti isomer) (6.4 g.) was obtained as an oil.

I.R. spectrum (Film): 1730, 1585 cm$^{-1}$.

N.M.R spectrum (CDCl$_3$, δ) ppm: 9.05 (1H, s), 4.43 (2H, q, J=7 Hz), 4.20 (3H, s), 1.40 (3H, t, J=7 Hz).

(3) Ethyl 2-methoxyimino-2-(1,2,5-thiadiazol-3-yl)acetate (anti isomer) (3.0 g.) was treated with 1N aqueous solution of sodium hydroxide (16.8 ml.) according to a similar manner to that of Example 1(a)(5) to give 2-methoxyimino-2-(1,2,5-thiadiazol-3-yl)acetic acid (anti isomer) (2.46 g. ), mp 110° to 111° C.

I.R. spectrum (Nujol): 2700–2100, 1700, 1560 cm$^{-1}$.

N.M.R. spectrum (d$_6$-DMSO, δ) ppm: 9.27 (1H, s), 4.07 (3H, s).

(b) Preparation of the object compound

2-Methoxyimino-2-(1,2,5-thiadiazol-3-yl)acetic acid (anti isomer) (1.87 g.) and 7-amino-3-(1,3,4-thiadiazol-2-yl)-thiomethyl-3-cephem-b 4-carboxylic acid (3.3 g.) were reacted according to a similar manner to that of Example 1(b) to give powder of 7-[2-methoxyimino-2-(1,2,5-thiadiazol-3-yl)acetamido]-3-(1,3,4-thiadiazol-2-yl)thiomethyl-3-cephem-4-carboxylic acid (anti isomer) (3.0 g.), mp 115° to 120° C. (dec.).

I.R. spectrum (Nujol): 3300, 1770, 1700, 1675, 1625, 1585 cm$^{-1}$.

N.M.R. spectrum (d$_6$-DMSO, δ) ppm: 9.6 (1H, s), 9.55 (1H, d, J=8 Hz), 9.30 (1H, s), 5.82 (1H, dd, J=5,8 Hz), 5.18 (1H, d, J=5 Hz), 4.42 (2H, AB$_q$, J=13 Hz), 4.10 (3H, s), 3.73 (2H, broad s).

EXAMPLE 6

(a) Preparation of the starting compound (1) A solution of sodium (1.01 g.) in absolute methanol (10 ml.) was dropwise added over 15 minutes with stirring and ice-cooling to a solution of methyl 2-(isothiazol-4-yl)acetate (6.30 g.) and isopentyl nitrite (10.6 g.) in absolute methanol (63 ml.). The mixture was stirred for 30 minutes at the same temperature and for 3 hours at ambient temperature. The reaction mixture was concentrated and the residue was poured into a mixture of ethyl acetate (50 ml.) and water (50 ml.) The aqueous layer was separated and the ethyl acetate layer was extracted twice with 1N aqueous solution of sodium hydroxide (20 ml. and 10 ml.). The extracts and the aqueous layer separated above were combined, adjusted to pH 1 with 10% hydrochloric acid and extracted twice with ethyl acetate (70 ml. and 50 ml.). The extracts were washed with a 5% aqueous solution of sodium bicarbonate and a saturated aqueous solution of sodium chloride and dried over magnesium sulfate. The solvent was distilled off under reduced pressure to give methyl 2-hydroxyimino-2-(isothiazol-4-yl)acetate (anti isomer) (4.55 g.), mp 110° to 112° C.

I.R. spectrum (Nujol): 3230, 1730 cm$^{-1}$.

(2) A mixture of methyl 2-hydroxyimino-2-(isothiazol-4-yl)-acetate (anti isomer) (3.41 g.), 36% aqueous solution of formaldehyde (24 ml.), conc. hydrochloric acid (12 ml.) and water (24 ml.) was stirred for 7 hours at 90° to 100° C. The reaction mixture was allowed to stand overnight in a refrigerator to precipitate crystals. The crystals were collected by filtration, washed with a small amount of ice-water and then dried to give 2-(isothiazol-4-yl)glyoxylic acid (2.09 g.). The mother liquor was extracted with ethyl acetate to give the same compound (0.34 g.), mp 145° to 148° C.

I.R. spectrum (Nujol): 1720, 1675 cm$^-$.

(3) A suspension of 2-(isothiazol-4-yl)glyoxylic acid (240 mg.), magnesium hydroxide (290 mg.) and hydroxylamino hydrochloride (140 mg.) in a mixture of ethanol (2 ml.) and water (10 ml.) was stirred for 2 hours at ambient temperature and allowed to stand overnight at ambient temperature. Ethanol was distilled off and to the residue was added ethyl acetate. The mixture was adjusted to pH 1 with 10% hydrochloric acid and the ethyl acetate layer was washed with water and dried over magnesium sulfate. The solvent was distilled off under reduced pressure to give 2-hydroxyimino-2-(isothiazol-4-yl)acetic acid (syn isomer) (0.20 g.), mp 159° to 161° C. (dec.).

I.R. spectrum (Nujol): 3250, 3200, 1690 cm$^{-1}$.

(4) Dichloroacetyl chloride (3.58 g.) was added with stirring and ice-cooling to a suspension of 2-hydroxyimino-2-(isothiazol-4-yl)acetic acid (syn isomer) (1.50 g.) in dry methylene chloride (40 ml.), and the mixture was stirred for 2 hours at the same temperature. The reaction mixture was concentrated to the volume of 10 ml. Petroleum ether (50 ml.) was added to the residue and the mixture was cooled in dry ice-acetone bath. Precipitates were collected by filtration and washed with petroleum ether to give 2-dichloroacetoxyimino-2-(isothiazol-4-yl)acetic acid (syn isomer) (1.20 g.).

(b) Preparation of the object compound

Thionyl chloride (770 mg.) was added to dimethylformamide (330 mg.), and the resultant was stirred for 30 minutes at 40° C. The mixture was concentrated by dryness and the residue was suspended in methylene chloride (40 ml.). 2-Dichloroacetoxyimino-2-(isothiazol-4-yl)acetic acid (syn isomer) (1.20 g.) was added thereto at −10° to −15° C., and the mixture was stirred for 30 minutes at the same temperature. In the other hand, a suspension of 7-amino-3-(1-methyl-1H-tetrazol-5-yl)thiomethyl-3-cephem-4-carboxylic acid (1.32 g.) and bis(trimethylsilyl)acetamide (3.2 g.) in dry methylene chloride (40 ml.) was stirred for 30 minutes at ambient temperature to give clear solution. This solution was at once added at −40° C. to the methylene chloride solution obtained above, and the mixture was stirred for 1 hour at −40° to −20° C. and for 1 hour at 0° to 5° C. The reaction mixture was concentrated, and to the residue containing 7-[2-dichloroacetoxyimino-2-(isothiazol-4-yl)acetamido]-3-(1-methyl-1H-tetrazol-5-yl)thiomethyl-3-cephem-4-carboxylic acid (syn isomer) were added ethyl acetate (100 ml.) and 5% hydrochloric acid (50 ml.). The ethyl acetate layer was separated, washed with water and dried over magnesium sulfate. The solvent was distilled off to give 7-[2-hydroxyimino-2-(isothiazol-4-yl)acetamido]-3-(1-methyl-1H-tetrazol-5-yl)thiomethyl-3-cephem-4-carboxylic acid (syn isomer) (860 mg.). This compound was dissolved in acetone (20 ml.) and the solution was chromatographed on activated charcoal using acetone as an eluent. Acetone was distilled off from the eluate, and the residue was pulverized with ether to give pure object compound (400 mg.), mp 113° to 116° C. (dec.).

I.R. spectrum (Nujol): 3250, 1790, 1700, 1660 cm$^{-1}$.

N.M.R. spectrum (d$_6$-acetone+D$_2$O, δ) ppm: 9.16 (1H, s), 8.78 (1H, s), 6.00 (1H, d, J=5 Hz), 5.25 (1H, d, J=5 Hz), 4.43 (2H, s), 4.00 (3H, s), 3.80 (2H, s).

EXAMPLE 7

(a) Preparation of the starting compound (1) A mixture of methyl 2-(1,2,5-thiadiazol-3-yl)acetate (25.0 g.) and selenium dioxide (52.6 g.) in a mixture of water (15.8 ml.) and dioxane (158 ml.) was stirred for 45 hours at 120° C. and precipitates were filtered off. The filtrate was concentrated under reduced pressure to give crude methyl 2-(1,2,5-thiadiazol-3-yl)glyoxylate. To this compound were added methanol (500 ml.) and 2N aqueous solution of sodium hydroxide (99 ml.). The mixture was stirred for 2.5 hours. Methanol was distilled off, and ethyl acetate and conc. hydrochloric acid were added thereto to acidify. The resulting mixture was extracted with ethyl acetate. The extract was washed, dried and concentrated. The residue (14.5 g.) was added to a solution of ethanol (920 ml.) and 1N aqueous solution of potassium hydroxide (92 ml.). The resultant mixture was stirred for 30 minutes, and precipitates were collected by filtration and washed with ethanol to give potassium 2-(1,2,5-thiadiazol-3-yl)glyoxylate. This compound was added to a mixture of conc. hydrochloric acid (10 ml.), water (30 ml.) and ethyl acetate (100 ml.), and extracted with the ethyl acetate. The aqueous layer was further extracted with ethyl acetate after salting-out. Both extracts were combined and an insoluble material was filtered off. The filtrate was dried over magnesium sulfate and concentrated to give 2-(1,2,5-thiadiazol-3-yl)glyoxylic acid (12 g.).

I.R. spectrum (Nujol): 1700 cm$^{-1}$.

N.M.R. spectrum (D$_2$O+KOH, δ) ppm: 8.7 (1H, s).

(2) 2-(1,2,5-Thiadiazol-3-yl)glyoxylic acid (7.4 g.) and hydroxylamine hydrochloride (3.1 g.) were reacted in the presence of magnesium hydroxide (4.7 g.) according to a similar manner to that of Example 6(a)(3) to give 2-hydroxyimino-2-(1,2,5-thiadiazol-3-yl)acetic acid (syn isomer) (7.5 g.).

I.R. spectrum (Nujol): 1700 cm$^{-1}$.

N.M.R. spectrum (d$_6$-acetone, δ) ppm: 9.08 (1H, s).

(3) 2-Hydroxyimino-2-(1,2,5-thiadiazol-3-yl)acetic acid (syn isomer) (4.8 g.) and dichloroacetyl chloride (9.2 g.) were reacted according to a similar manner to that of Example 6(a)(4) to give crystals of 2-dichloroacetoxyimino-2-(1,2,5-thiadiazol-3-yl)acetic acid (syn isomer) (3.7 g.).

I.R. spectrum (Nujol): 1780, 1755 cm$^{-1}$.

(b) Preparation of the object compound

Phosphorus pentachloride (2.5 g.) was added with stirring and ice-cooling to a suspension of 2-dichloroacetoxyimino-2-(1,2,5-thiadiazol-3-yl)acetic acid (syn isomer) (3.7 g.) in dry methylene chloride (100 ml.), and the mixture was stirred for 1 hour at ambient temperature. The resultant mixture was concentrated and benzene was added thereto and distilled off (twice repeated). The residue was dissolved in dry methylene chloride. The solution was dropwise added with stirring and ice-cooling to a solution of 7-amino-3-(1-methyl-1H-tetrazol-5-yl)thiomethyl-3-cephem-4-carboxylic acid (3.9 g.) and bis(trimethylsilyl)acetamide (12 ml.) in dry methylene chloride (200 ml.). The resultant mixture was stirred for 1 hour at the same temperature and for 1 hour at ambient temperature. Methylene chloride was distilled off and to the residue were added ethyl acetate and water. After an insoluble material was filtered off, the ethyl acetate layer in the filtrate was washed three times with water, with a saturated aqueous solution of sodium chloride and dried over magnesium sulfate. The solvent was distilled off to give a residue (4.5 g.). The residue containing 7-[2-dichloroacetoxyimino-2-(1,2,5-thiadiazol-3-yl)acetamido]-3-(1-methyl-1H-tetrazol-5-yl)thiomethyl-3-cephem-4-carboxylic acid (syn isomer) was dissolved in a mixture of water and acetone, and the solution was stirred for 2 hours at ambient temperature and extracted with ethyl acetate. The extract was washed with water and with a saturated aqueous solution of sodium chloride, and dried over magnesium sulfate. The solvent was distilled off and the residue was dissolved in ethyl acetate. The solution was chromatographed on silica gel (5 g.) and the eluate was concentrated. The residue was reprecipitated from a mixture of ethyl acetate and ether, and the precipitates were collected by filtration, washed with ether and dried (3 g.). The powder was dissolved in distillated acetone, and the solution was treated with activated charcoal (3 g.) in column and then concentrated. The residue was reprecipitated from a mixture of acetone and ether. The precipitates was collected by filtration, washed with ether and dried to give 7-[2-hydroxyimino-2-(1,2,5-thiadiazol-3-yl)acetamido]-3-(1-methyl-1H-tetrazol-5-yl)thiomethyl-3-cephem-4-carboxylic acid (syn isomer) (2.5 g.), mp 155° to 160° C. (dec.).

N.M.R. spectrum ($d_6$-acetone+$D_2O$, δ) ppm: 9.00 (1H, s), 5.30 (1H, d, J=4.5 Hz), 5.07 (1H, d, J=4.5 Hz), 4.43 (2H, s), 4.03 (3H, s), 3.87 (2H, s).

EXAMPLE 8

Dimethylformamide (0.43 g.) was added to dry ethyl acetate (2 ml.), and phosphorus oxychloride (0.9 g.) was added thereto with stirring under 10° C. To the mixture were added dry ethyl acetate (10 ml.) and 2-methoxyimino-2-(1,2,3-thiadiazol-4-yl)acetic acid (anti isomer) (1 g.) at 0° C., after which the resulting mixture was stirred for 30 minutes at the same temperature. On the other hand, trimethylsilylacetamide (6 g.) was added to a suspension of 7-aminocephalosporanic acid (1.58 g.) in dry ethyl acetate (30 ml.) and the resulting mixture was stirred for 1 hour at 40° C. to give clear solution. To this solution was dropwise added at −20° C. the above obtained ethyl acetate solution, after which the mixture was stirred for 1 hour at the same temperature. Water (20 ml.) was added thereto and the ethyl acetate layer was separated after shaking the mixture. The ethyl acetate layer was washed with water, and water (30 ml.) was added thereto. The mixture was adjusted to pH 7.5 with sodium bicarbonate and extracted. The aqueous layer was separated and ethyl acetate (50 ml.) was added thereto. The resulting mixture was adjusted to pH 2 with stirring with diluted hydrochloric acid and extracted with ethyl acetate. The extract was washed with water and with a saturated aqueous solution of sodium chloride, and dried over magnesium sulfate. The solution was treated with activated charcoal and concentrated under reduced pressure. The residue was pulverized with ether and, the powder was collected by filtration and dried to give pale yellow powder of 7-[2-methosyimino-2-(1,2,3-thiadiazol-4-yl)acetamido]cephalosporanic acid (anti isomer) (0.8 g.).

I.R. spectrum (Nujol): 3300, 1780, 1730, 1680, 1640 cm$^{-1}$.

N.M.R. spectrum ($d_6$-DMSO, δ) ppm: 9.72 (1H, s), 9.60 (1H, d, J=8 Hz), 5.88 (1H, dd, J=5,8 Hz), 5.23 (1H, d, J=5 Hz), 4.87 (2H, AB$_q$, J=13 Hz), 4.07 (3H, s), 3.60 (2H, AB$_q$, J=17 Hz), 2.04 (3H, s).

EXAMPLE 9

2-Methoxyiminio-2-(1,2,3-thiadiazol-4-yl)acetic acid (anti isomer) (1.0 g.) and 7-amino-3-(5-methyl-1,3,4-thiadiazol-2-yl)thiomethyl-3-cephem-4-carboxylic acid (2.16 g.) were reacted according to similar manners to those of Examples 1(b) and 8 to give pale yellow powder of 7-[2-methoxyimino-2-(1,2,3-thiadiazol-4-yl)acetamido]-3-(5-methyl-1,3,4-thiadiazol-2-yl)thiomethyl-3-cephem-4-carboxylic acid (anti isomer) (1.68 g.), mp 104° to 115° C. (dec.).

I.R. spectrum (Nujol): 3350, 1785, 1730 cm$^{-1}$.

N.M.R. spectrum ($d_6$-DMSO, δ) ppm: 9.72 (1H, s), 9.61 (1H, d, J=8 Hz), 5.84 (1H, dd, J=5,8 Hz), 5.15 (1H, d, J=5 Hz), 4.38 (2H, AB$_q$, J=13 Hz), 4.07 (3H, s), 3.70 (2H, broad s), 2.67 (3H, s).

EXAMPLE 10

2-Methoxyimino-2-(1,2,3-thiadiazol-4-yl)acetic acid (anti isomer) (1 g.) and 7-amino-3-(1-methyl-1H-tetrazol-5-yl)thiomethyl-3-cephem-4-carboxylic acid (1.9 g.) were reacted according to similar manners to those of Examples 1(b) and 8 to give pale yellow powder of 7-[2-methoxyimino-2-(1,2,3-thiadiazol-4-yl)acetamido]-3-(1-methyl-1H-tetrazol-5-yl)thiomethyl-3-cephem-4-carboxylic acid (anti isomer) (1.5 g.).

I.R. spectrum (Nujol): 3300, 1790, 1730, 1690, 1630 cm$^{-1}$.

N.M.R. spectrum ($d_6$-DMSO, δ) ppm: 9.78 (1H, s), 9.66 (1H, d, J=8 Hz), 5.83 (1H, dd, J=5,8 Hz), 5.17 (1H, d, J=5 Hz), 4.33 (2H, broad s), 4.10 (3H, s), 3.93 (3H, s), 3.69 (2H, broad s).

EXAMPLE 11

(a) Preparation of the starting compound (1) A mixture of ethyl 2-hydroxyimino-2-(1,2,5-thiadiazol-3-yl)acetate (a mixture of syn and anti isomers) (6.0 g.), 36% aqueous solution of formaldehyde (40 ml.), conc. hydrochloric acid (20 ml.) and water (40 ml.) was treated according to a similar manner to that of Example 6(a)(2) to give crystals of 2-(1,2,5-thiadiazol-3-yl)glyoxylic acid (1.6 g.), mp 130° to 133° C.

(2)(i) Phenolphthalein indicator (3 drops) was added to a solution of O-methylhydroxylamine hydrochloride (0.95 g.) in dry methanol (10 ml.). To the solution was dropwise added with stirring at ambient temperature 1N methanol solution of sodium methoxide (11 ml.)

until the color of the solution was changed to purplish red. O-Methylhydroxylamine hydrochloride was added thereto by small portions until the solution was changed to colorless solution. The mixture was stirred for 30 minutes at ambient temperature. After precipitating sodium chloride was filtered off, 2-(1,2,5-thiadiazol-3-yl)glyoxylic acid (1.5 g.) was added to the filtrate and the mixture was stirred for 50 minutes at ambient temperature. After methanol was distilled off at low temperature, water was added to the residue. The mixture was adjusted to pH 7.5 with an aqueous solution of sodium bicarbonate and washed with ether. The aqueous layer was adjusted to pH 1.5 with 10% hydrochloric acid, subjected to salting-out and extracted with ether. The extract was washed with a saturated aqueous solution of sodium chloride and dried over magnesium sulfate. Ether was distilled off at low temperature to give 2-methoxyimino-2(1,2,5-thiadiazol-3-yl)acetic acid (a mixture of syn and anti isomers) (1.5 g.)

(ii) This material was dissolved in ether (15 ml.) and a solution of diazomethane in ether was gradually added thereto under ice-cooling until the color of the mixture was changed to yellow. Acetic acid was immediately added thereto and the mixture was washed with a sodium bicarbonate aqueous solution and a saturated sodium chloride aqueous solution and dried over magnesium sulfate. Ether was distilled off to give oily residue. The oily residue was chromatographed on silica gel using benzene as an eluent. Firstly the eluate containing syn isomer was eluted and the eluate was collected and concentrated to give oily methyl 2-methoxyimino-2-(1,2,5-thiadiazol-3-yl)acetate (syn isomer) (0.9 g.).

I.R. spectrum (Film): 1740, 1590 cm$^{-1}$.

N.M.R. spectrum (CDCl$_3$, δ) ppm: 8.92 (1H, s), 4.09 (3H, s), 3.96 (3H, s).

After the eluate containing syn isomer was eluted, then the eluate containing anti isomer was eluted. The eluate was collected and concentrated to give oily methyl 2-methoxyimino-2-(1,2,5-thiadiazol-3-yl)acetate (anti isomer) (0.5 g.).

I.R. spectrum (Film: 1740, 1590 cm$^{-1}$.

(iii) An aqueous solution of 1N sodium hydroxide (5.4 ml.) was added with stirring at ambient temperature to a solution of methyl 2-methoxyimino-2-(1,2,5-thiadiazol-3-yl)acetate (syn isomer) (0.9 g.) in methanol (10 ml.) and the mixture was stirred for 1 hour at ambient temperature. Methanol was distilled off and water was added to the residue, after which the mixture was washed with ether. The aqueous layer was adjusted to pH 1.5 with 10% hydrochloric acid, subjected to salting-out and extracted with ether. The extract was washed with a saturated aqueous solution of sodium chloride and dried over magnesium sulfate. Ether was distilled off. Benzene was added to the residue and removed to give crystals of 2-methoxyimino-2-(1,2,5-thiadiazol-3-yl)acetic acid (syn isomer) (0.67 g.), mp 99° to 100° C.

I.R. spectrum (Nujol): 2650–2150, 1735, 1690, 1600 cm$^{-1}$.

N.M.R. spectrum (d$_6$-DMSO, δ) ppm: (9.15 (1H, s), 4.05 (3H, s).

(b) Preparation of the object compound

2-Methoxyimino-2-(1,2,5-thiadiazol-3-yl)acetic acid (syn isomer) (0.6 g.) and 7-amino-3-(1,3,4-thiadiazol-2-yl)thiomethyl-3-cephem-4-carboxylic acid (1.16 g.) were reacted according to similar manners to those of Examples 12 and 15 to give 7-[2-methoxyimino-2-(1,2,5-thiadiazol-3-yl)acetamido]-3-(1,3,4-thiadiazol-2-yl)thiomethyl-3-cephem-4-carboxylic acid (syn isomer) (1.10 g.), mp 111° to 120° C.

I.R. spectrum (Nujol): 3300, 1770, 1725, 1670, 1620, 1550 cm$^{-1}$.

N.M.R. spectrum (d$_6$-DMSO, δ) ppm: 9.77 (1H, d, J=8 Hz), 9.58 (1H, s), 9.13 (1H, s), 5.85 (1H, dd, J=5,8 Hz), 5.18 (1H, d, J=5 Hz), 4.43 (2H, AB$_q$, J=13 Hz), 4.02 (3H, s), 3.68 (2H, broad s).

EXAMPLE 12

Dimethylformamide (0.34 g) was added to dry ethyl acetate (1 ml), and then phosphorus oxychloride (0.72 g) was added thereto under 10° C. The mixture was stirred at −5° C. to solidify. Dry ethyl acetate (10 ml) was added thereto and 2-methoxyimino-2-(1,2,3-thiadiazol-4-yl)acetic acid (syn isomer)(0.8 g) was added to the mixture at 0° C., after which the resulting mixture was stirred for 30 minutes at the same temperature. On the other hand, trimethylsilylacetamide (4.9 g) was added to a suspension of 7-aminocephalosporanic acid (1.28 g) in dry ethyl acetate (30 ml), and the mixture was stirred for 1 hour at 40° C. to give a clear solution. To this solution was dropwise added at −20° C. the above-obtained ethyl acetate solution, and the mixture was stirred for 1 hour at the same temperature. Water (20 ml) was added to the reaction mixture, and the resulting mixture was shaken enough. The ethyl acetate layer was separated, washed with water and water (30 ml) was added to the ethyl acetate solution. The mixture was adjusted to pH 7.5 with sodium bicarbonate and washed with ethyl acetate. The aqueous layer was adjusted to pH 2 with dilute hydrochloric acid with stirring after addition of ethyl acetate (50 ml). The ethyl acetate layer was washed with water and with a saturated aqueous solution of sodium chloride, and dried over magnesium sulfate. After treating with activated charcoal, the solvent was distilled off under reduced pressure. The residue was pulverized with ether to give pale yellow powder of 7-[2-methylimino-2-(1,2,3-thiadiazol-4-yl)acetamido]cephalosporanic acid (syn isomer)(1.2 g).

I.R. spectrum (Nujol): 3300, 1790, 1735, 1680 cm$^{-1}$.

N.M.R. spectrum (d$_6$-DMSO, δ) 9.83 (1H, d, J=8 Hz), 9.40 (1H, s), 5.86 (1H, dd, J=5,8 Hz), 5.18 (1H, d, J=5 Hz), 4.83 (2H, AB$_q$, J=14 Hz), 3.97 (3H, s), 3.55 (2H, broad s), 2.00 (3H, s).

EXAMPLE 13

2-Methoxyimino-2-(1,2,3-thiadiazol-4-yl)acetic acid (syn isomer)(3.74 g) and 7-amino-3-methyl-3-cephem-4-carboxylic acid (4.3 g) were reacted according to similar manners to those of Examples 12 and 15 to give 7-[2-methoxyimino-2-(1,2,3-thiadiazol-4-yl)acetamido]-3-methyl-3-cephem-4-carboxylic acid (syn isomer)(5.0 g), mp 111° to 116° C. (dec.).

I.R. spectrum (Nujol): 3300, 1785, 1720, 1660, 1600, 1548 cm$^{-1}$.

N.M.R. spectrum (d$_6$-DMSO, δ): 9.77 (1H, d, J=8 Hz), 9.37 (1H, s), 5.78 (1H, dd, J=5,8 Hz) 5.11 (1H, d, J=5 Hz), 3.97 (3H, s), 3.45 (2H, AB$_q$, J=17 Hz), 2.00 (3H, s).

EXAMPLE 14

2-Methoxyimino-2-(1,2,3-thiadiazol-4-yl)acetic acid (syn isomer)(0.65 g) and 7-amino-3-carbamoyloxymethyl-3-cephem-4-carboxylic acid (0.96 g) were reacted according to similar manners to those of Examples 12 and 15 to give 7-[2-methoxyimino-2-(1,2,3-thiadiazol-4-yl)acetamido]-3-carbamoyloxymethyl-3-cephem-4-carboxylic acid (syn isomer)(0.7 g).

I.R. spectrum (Nujol): 3250, 1780, 1720, 1670 cm$^{-1}$.

N.M.R. spectrum (d$_6$-DMSO, δ): 9.77 (1H, d, J=9 Hz), 9.36 (1H, s), 6.54 (2H, s), 5.87 (1H, dd, J=5,9 Hz), 5.16 (1H, d, J=5 Hz), 4.74 (2H, AB$_q$, J=13 Hz), 3.96 (3H, s), 3.51 (2H, broad s).

EXAMPLE 15

Dimethylformamide (0.34 g.) was added to dry ethyl acetate (1 ml.), and then phosphorus oxychloride (0.72 g.) was added thereto under 10° C. The mixture was stirred at −5° C. to solidify. Dry ethyl acetate (10 ml.) was added thereto and 2-methoxyimino-2-(1,2,3-thiadiazol-4-yl)acetic acid (syn isomer) (0.8 g.) was added to the mixture at 0° C., after which the resulting mixture was stirred for 30 minutes at the same temperature. On the other hand, trimethylsilylacetamide (4.9 g.) was added to a suspension of 7-amino-3-(1-methyl-1H-tetrazol-5-yl)thiomethyl-3-cephem-4-carboxylic acid (1.54 g.) in dry ethyl acetate (30 ml.), and the mixture was stirred for 1 hour at 40° C. to give a clear solution. To this solution was added dropwise at −20° C. the above-obtained ethyl acetate solution, and the mixture was stirred for 1 hour at the same temperature. The reaction mixture was post-treated according to a similar manner to that of Example 12 to give pale yellow powder of 7-[2-methoxyimino-2-(1,2,3-thiadiazol-4-yl)acetamido]-3-(1-methyl-1H-tetrazol-5-yl)thiomethyl-3-cephem-4-carboxylic acid (syn isomer) (0.9 g.).

I.R. spectrum (Nujol): 3300, 1780, 1730, 1680, 1630 cm$^{-1}$.

N.M.R. spectrum (d$_6$-DMSO, δ) ppm: 9.89 1H, d, J=8 Hz), 9.40 (1H, s), 5.88 (1H, dd, J=5,8 Hz), 5.20 (1H, d, J=5 Hz), 4.33 (2H, broad s), 4.01 (3H, s), 3.93 (3H, s), 3.73 (2H, broad s).

EXAMPLE 16

2-Methoxyimino-2-(1,2,3-thiadiazol-4-yl)acetic acid (syn isomer) (350 mg.) and 7-amino-3-[1-(2-dimethylaminoethyl)-1H, tetrazol-5-yl)thiomethyl-3-cephem-4-carboxylic acid (600 mg.) were reacted according to similar manners to those of Examples 12 and 15 to give 7-[2-methoxyimino-2-(1,2,3-thiadiazol-4-yl)acetamido]-3-[1-(2-dimethylaminoethyl)-1H-tetrazol-5-yl]thiomethyl-3-cephem-4-carboxylic acid (syn isomer) (230 mg.).

I.R. spectrum (Nujol): 1775, 1670, 1605 cm$^{-1}$.

N.M.R. spectrum (d$_6$-DMSO, δ) ppm: 9.85 (1H, d, J=8 Hz), 9.43 (1H, s), 5.83 (1H, dd, J=5,8 Hz), 5.15 (1H, d, J=5 Hz), 4.37 (2H, t, J=5 Hz), 4.30 (2H, broad s), 3.98 (3H, s), 3.65 (2H, broad s), 3.05 (2H, t, J=5 Hz), 2.38 (6H, s).

EXAMPLE 17

Dicyclohexylcarbodiimide (0.99 g.) was added at ambient temperature to a solution of diphenylmethyl 7-amino-7-methoxy-3-(1-methyl-1H-tetrazol-5-yl)thiomethyl-3-cephem-4-carboxylate (2.1 g.) in dry tetrahydrofuran (20 ml.) and then 2-methoxyimino-2-(1,2,3-thiadiazol-4-yl)acetic acid (syn isomer) (0.9 g) was added thereto at ambient temperature to give white precipitates. After stirring for 2 days at ambient temperature, the precipitates were filtered off and the filtrate was concentrated under reduced pressure to give brown oil. The oil as subjected to column chromatography on silica gel, eluted with a mixture of chloroform and ethyl acetate and the eluate was concentrated under reduced pressure to give diphenylmethyl 7-[2-methoxyimino-2-(1,2,3-thiadiazol-4-yl)acetamido]-7-methoxy-3-(1-methyl-1H-tetrazol-5-yl)thiomethyl-3-cephem-4-carboxylate (syn isomer) (1.78 g.).

I.R. spectrum (Nujol) 3300, 1780, 1720, 1690 cm$^{-1}$.

N.M.R. spectrum (d$_6$-DMSO, δ) ppm: 10.24 (1H, s), 9.37 (1H, s), 7.06–7.72 (10H, m), 6.82 (1H, s), 5.19 (1H, s), 4.22 (2H, broad s), 3.94 (3H, s), 3.79 (3H, s), 3.64 (2H, broad s), 3.48 (3H, s).

EXAMPLE 18

Anisole (0.86 ml.) was added at ambient temperature to a solution of diphenylmethyl 7-[2-methoxyimino-2-(1,2,3-thiadiazol-4-yl)acetamido]-7-methoxy-3-(1-methyl-1H-tetrazol-5-yl)thiomethyl-3-cephem-4-carboxylate (syn isomer) (0.86 g.) in dry 1,2-dichloroethane (10 ml.), and then trifluoroacetic acid (1.68 g.) was added dropwise thereto under ice-cooling. The resulting mixture was stirred for 2 hours under ice-cooling and the reaction mixture was concentrated under reduced pressure. To the residue were added ethyl acetate (20 ml.) and water (20 ml.). After shaking the mixture, the ethyl acetate layer was separated. The remaining aqueous layer was further extracted with ethyl acetate (10 ml. and 5 ml.). The ethyl acetate layers were combined and 10% aqueous solution of dipotassium hydrogen phosphate (20 ml.) was added thereto. The mixture was shaken and the aqueous layer was separated. The ethyl acetate layer was further extracted with 10% aqueous solution of dipotassium hydrogen phosphate (10 ml. and 5 ml.). The aqueous layers were combined and washed in turn with ethyl acetate (10 ml. and 5 ml.) and ether (10 ml.). Two remaining solvent in the aqueous layer was removed by bubbling of nitrogen gas. The resulting aqueous layer was adjusted to pH 2 with 10% hydrochloric acid under ice-cooling. Precipitates were collected by filtration, washed with water and dried over phosphorus pentoxide under reduced pressure to give 7-[2-methoxyimino-2-(1,2,3-thiadiazol-4-yl)acetamido]-7-methoxy-3-(1-methyl-1H-tetrazol-5-yl)thiomethyl-3-cephem-4-carboxylic acid (syn isomer) (0.21 g.).

I.R. spectrum (Nujol): 3250, 1780, 1730, 1690 cm$^{-1}$.

N.M.R. spectrum (d$_6$-DMSO, δ) ppm: 10.22 (1H, s), 9.27 (1H, s), 5.17 (1H, s), 4.22, 4.4 (2H, AB$_q$, J=13 Hz), 4.01 (3H, s), 3.94 (3H, s), 3.90 (2H, s), 3.52 (3H, s).

EXAMPLE 19

The following compounds were obtained according to a similar manner to that of Example 18.

(1) 7-[2-Methoxyimino-2-(1,2,3-thiadiazol-4-yl)acetamido]-3-(1,3,4-thiadiazol-2-yl)thiomethyl-3-cephem-4-carboxylic acid (anti isomer).

I.R. spectrum (Nujol): 3150, 1760, 1705, 1660, 1590, 1530 cm$^{-1}$.

N.M.R. spectrum (d$_6$-DMSO, δ) ppm: 9.68 (1H, s), 9.58 (1H, d, J=8 Hz), 9.51 (1H, s), 5.84 (1H, dd, J=5, 8 Hz), 5.20 (1H, d, J=5 Hz), 4.45 (2H, AB$_q$, J=13 Hz), 4.07 (3H, s), 3.72 (2H, AB$_q$, J=17 Hz).

(2) 7-[2-Methoxyimino-2-(1,2,3-thiadiazol-4-yl)-acetamido]-3-(1,3,4-thiadiazol-2-yl)thiomethyl-3-cephem-4-carboxylic acid (syn isomer), mp 90° to 98° C. (dec.).

I.R. spectrum (Nujol): 3250, 1780, 1725, 1680, 1530 cm$^{-1}$.

N.M.R. spectrum (d$_6$-DMSO, δ) ppm: 9.82 (1H, d, J=8 Hz), 9.51 (1H, s), 9.37 (1H, s), 5.88 (1H, dd, J=5, 8 Hz), 5.20 (1H, d, J=5 Hz), 4.44 (2H, AB$_q$, J=13 Hz), 3.99 (3H, s), 3.72 (2H, AB$_q$, J=17 Hz).

(3) 7-[2-Methoxyimino-2-(5-methyl-1,3,4-thiadiazol-2-yl)acetamido]-3-(1,3,4-thiadiazol-2-yl)thiomethyl-3-cephem-4-carboxylic acid (syn isomer), mp. 175° to 178° C. (dec.).

I.R. spectrum (Nujol): 3250, 1785, 1700, 1665, 1620, 1590, 1550 cm$^{-1}$

N.M.R. spectrum (d$_6$-DMSO, δ) ppm: 9.83 (1H, d, J=8 Hz), 9.57 (1H, s), 5.87 (1H, dd, J=5, 8 Hz), 5.18 (1H, d, J=5 Hz), 4.43 (2H, AB$_q$, J=13 Hz), 4.00 (3H, s), 3.70 (2H, AB$_q$, J=17 Hz), 2.77 (3H, s).

(4) 7-[2-Methoxyimino-2-(5-methyl-1,3,4-thiadiazol-2-yl)acetamido]-3-(1,3,4-thiadiazol-2-yl)thiomethyl-3-cephem-4-carboxylic acid (anti isomer), mp. 110° to 115° C. (dec.).

I.R. spectrum (Nujol): 3200, 1780, 1730, 1680, 1630, 1530 cm$^{-1}$.

N.M.R. spectrum (d$_6$-DMSO, δ) ppm: 9.74 (1H, d, J=8 Hz), 9.52 (1H, s), 5.86 (1H, dd, J=5, 8 Hz), 5.20 (1H, d, J=5 Hz), 4.45 (2H, AB$_q$, J=13 Hz), 4.10 (3H, s), 3.72 (2H, AB$_q$, J=17 Hz), 2.90 (3H, s).

(5) 7-[2-Methoxyimino-2-(1,2,5-thiadiazol-3-yl)acetamido]-3-(1,3,4-thiadiazol-2-yl)thiomethyl-3-cephem-4-carboxylic acid (anti isomer), mp 115° to 120° C. (dec.).

I.R. spectrum (Nujol): 3300, 1770, 1700, 1675, 1625, 1585 cm$^{-1}$.

N.M.R. spectrum (d$_6$-DMSO, δ) ppm: 9.6 (1H, s), 9.55 (1H, d, J=8 Hz), 9.30 (1H, s), 5.82 (1H, dd, J=5, 8 Hz), 5.18 (1H, d, J=5 Hz), 4.42 (2H, AB$_q$, J=13 Hz), 4.10 (3H, s), 3.73 (2H, broad s).

(6) 7-[2-Hydroxyimino-2-(isothiazol-4-yl)acetamido]-3-(1-methyl-1H-tetrazol-5-yl)thiomethyl-3-cephem-4-carboxylic acid (syn isomer).

I.R. spectrum (Nujol): 3250, 1790, 1700, 1660 cm$^{-1}$.

N.M.R. spectrum (d$_6$-acetone+D$_2$O, δ) ppm: 9.16 (1H, s), 8.78 (1H, s), 6.00 (1H, d, J=5 Hz), 5.25 (1H, d, J=5 Hz), 4.43 (2H, s), 4.00 (3H, s), 3.80 (2H, s).

(7) 7-[2-Hydroxyimino-2-(1,2,5-thiadiazol-3-yl)acetamido]-3-(1-methyl-1H-tetrazol-5-yl)thiomethyl-3-cephem-4-carboxylic acid (syn isomer), mp 155° to 160° C. (dec.).

N.M.R. spectrum (d$_6$-acetone+D$_2$O, δ) ppm: 9.00 (1H, s), 5.30 (1H, d, J=4.5 Hz), 5.07 (1H, d, J=4.5 Hz), 4.43 (2H, s), 4.03 (3H, s), 3.87 (2H, s).

(8) 7-[2-Methoxyimino-2-(1,2,3-thiadiazol-4-yl)acetamido]cephalosporanic acid (anti isomer).

I.R. spectrum (Nujol): 3300, 1780, 1730, 1680, 1640 cm$^{-1}$.

N.M.R. spectrum (d$_6$-DMSO, δ) ppm: 9.72 (1H, s), 9.60 (1H, d, J=8 Hz), 5.88 (1H, dd, J=5, 8 Hz), 5.23 (1H, d, J=5 Hz), 4.87 (2H, AB$_q$, J=13 Hz), 4.07 (3H, s), 3.60 (2H, AB$_q$, J=17 Hz), 2.04 (3H, s).

(9) 7-[2-Methoxyimino-2-(1,2,3-thiadiazol-4-yl)acetamido]-3-(5-methyl-1,3,4-thiadiazol-2-yl)thiomethyl-3-cephem-4-carboxylic acid (anti isomer), mp. 104° to 115° C. (dec.).

I.R. spectrum (Nujol): 3350, 1785, 1730 cm$^{-1}$.

N.M.R. spectrum (d$_6$-DMSO, δ) ppm: 9.72 (1H, s), 9.61 (1H, d, J=8 Hz), 5.84 (1H, dd, J=5, 8 Hz), 5.15 (1H, d, J=5 Hz), 4.38 (2H, AB$_q$, J=13 Hz), 4.07 (3H, s), 3.70 (2H, broad s), 2.67 (3H, s).

(10) 7-[2-Methoxyimino-2-(1,2,3-thiadiazol-4-yl)acetamido]-3-(1-methyl-1H-tetrazol-5-yl)thiomethyl-3-cephem-4-carboxylic acid (anti isomer).

I.R. Spectrum (Nujol): 3300, 1790, 1730, 1690, 1630 cm$^{-1}$.

N.M.R. spectrum (d$_6$-DMSO, δ) ppm: 9.78 (1H, s), 9.66 (1H, d, J=8 Hz), 5.83 (1H, dd, J=5, 8 Hz), 5.17 (1H, d, J=5 Hz), 4.33 (2H, broad s), 4.10 (3H, s), 3.93 (3H, s), 3.69 (2H, broad s).

(11) 7-[2-Methoxyimino-2-(1,2,5-thiadiazol-3-yl)acetamido]-3-(1,3,4-thiadiazol-2-yl)thiomethyl-3-cephem-4-carboxylic acid (syn isomer), mp. 111° to 120° C.

I.R. spectrum (Nujol): 3300, 1770, 1725, 1670, 1620, 1550 cm$^{-1}$.

N.M.R. spectrum (d$_6$-DMSO, δ) ppm: 9.77 (1H, d, J=8 Hz), 9.58 (1H, s), 9.13 (1H, s), 5.85 (1H, dd, J=5, 8 Hz), 5.18 (1H, d, J=5 Hz), 4.43 (2H, AB$_q$, J=13 Hz), 4.02 (3H, s), 3.68 (2H, broad s).

(12) 7-[2-Methoxyimino-2-(1,2,3-thiadiazol-4-yl)acetamido]cephalosporanic acid (syn isomer).

I.R. spectrum (Nujol): 3300, 1790, 1735, 1680 cm$^{-1}$.

N.M.R. spectrum (d$_6$-DMSO, δ): 9.83 (1H, d, J=8 Hz), 9.40 (1H, s), 5.86 (1H, dd, J=5, 8 Hz), 5.18 (1H, d, J=5 Hz), 4.83 (2H, AB$_q$, J=14 Hz), 3.97 (3H, s), 3.55 (2H, broad s), 2.00 (3H, s).

(13) 7-[2-Methoxyimino-2-(1,2,3-thiadiazol-4-yl)acetamido]-3-methyl-3-cephem-4-carboxylic acid (syn isomer), mp 111° to 116° C. (dec.).

I.R. spectrum (Nujol): 3300, 1785, 1720, 1660, 1600 1548 cm$^{-1}$.

N.M.R. spectrum (d$_6$-DMSO, δ): 9.77 (1H, d, J=8 Hz), 9.37 (1H, s), 5.78 (1H, dd, J=5, 8 Hz), 5.11 (1H, d, J=5 Hz), 3.97 (3H, s), 3.45 (2H, AB$_q$, J=17 Hz), 2.00 (3H, s).

(14) 7-[2-Methoxyimino-2-(1,2,3-thiadiazol-4-yl)acetamido]-3-carbamoyloxymethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ): 9.77 (1H, d, J=9 Hz), 9.36 (1H, s), 6.54 (2H, s), 5.87 (1H, dd, J=5, 9 Hz), 5.16 (1H, d, J=5 Hz), 4.74 (2H, AB$_q$, J=13 Hz), 3.96 (3H, s), 3.51 (2H, broad s).

(15) 7-[2-Methoxyimino-2-(1,2,3-thiadiazol-4-yl)acetamido]-3-(1-methyl-1H-tetrazol-5-yl)thiomethyl-3-cephem-4-carboxylic acid (syn isomer)

I.R. spectrum (Nujol): 3300, 1780, 1730, 1680, 1630 cm$^{-1}$.

N.M.R. spectrum (d$_6$-DMSO, δ) ppm 9.89 (1H, d, J=8 Hz), 9.40 (1H, s), 5.88 (1H, dd, J=5, 8 Hz), 5.20 (1H, d, J=5 Hz), 4.33 (2H, broad s), 4.01 (3H, s), 3.93 (3H, s), 3.73 (2H, broad s).

(16) 7-[2-Methoxyimino-2-(1,2,3-thiadiazol-4-yl)acetamido]-3-[1-(2-dimethylaminoethyl)-1H-tetrazol-5-yl]thiomethyl-3-cephem-4-carboxylic acid (syn isomer).

I.R. spectrum (Nujol): 1775, 1670, 1605 cm$^{-1}$.

N.M.R. spectrum (d$_6$-DMSO, δ) ppm: 9.85 (1H, d, J=8 Hz), 9.43 (1H, s), 5.83 (1H, dd, J=5, 8 Hz), 5.15 (1H, d, J=5 Hz), 4.37 (2H, t, J=5 Hz), 4.30 (2H, broad s), 3.98 (3H, s), 3.65 (2H, broad s), 3.05 (2H, t, J=5 Hz), 2.38 (6H, s).

EXAMPLE 20

(a) Preparation of the Starting Compound (1) Ethyl 2-methoxyimino-2-(2-aminothiazol-4-yl)acetate (syn isomer) (11.5 g) was added at 65° C. to a solution of tert-butyl nitrite (7.7 g) in dimethyl-formamide (30 ml) and the mixture was stirred for 30 minutes at the same temperature. The reaction mixture was poured into water (150 ml) and the resultant mixture was extracted with ethyl acetate (100 ml). The extract was washed with a saturated aqueous solution of sodium chloride, dried over magnesium sulfate and evaporated under reduced pressure. The residue was purified by column chromatography on silica gel to give ethyl 2-methoxyimino-2-(4-thiazolyl)acetate(syn isomer) (1.3 g).

IR (film): 1730, 1600, 1500 cm$^{-1}$.

NMR (CDCl$_3$, δ): 1.4 (3H, t, J=7 Hz), 4.17 (3H, s), 4.48 (2H, q, J=7 Hz), 7.75 (1H, d, J=2 Hz), 8.92 (1H, d, J=2 Hz).

(2) An 1N aqueous solution of sodium hydroxide (9.1 ml) was added to a solution of ethyl 2-methoxyimino-2-(4-thiazolyl)acetate(syn isomer)(1.3 g) in methanol (15 ml) at ambient temperature and the mixture was stirred for 3.5 hours at ambient temperature. The reaction mixture was evaporated and the residue was dissolved in a saturated aqueous solution of sodium bicarbonate (10 ml). The solution was washed with ethyl acetate (15 ml) and acidified to pH 3.5 with 10% hydrochloric acid to give precipitates, which were collected by filtration to give colorless powder of 2-methoxyimino-2-(4-thiazolyl)acetic acid (syn isomer) (0.6 g).

IR (Nujol): 1730, 1600, 1550 cm$^{-1}$

NMR (d$_6$-DMSO, δ): 3.97 (3H, s), 8.08 (1H, d, J=2 Hz), 9.22 (1H, d, J=2 Hz).

(b) Preparation of the Object Compound

To dimethylformamide (0.2 g) was added dropwise phosphorus oxychloride (0.4 g) under stirring and ice-cooling, and the mixture was stirred for 30 minutes at 40° C. and then suspended in ethyl acetate (10 ml). To the suspension was added 2-methoxyimino-2-(4-thiazolyl)acetic acid (syn isomer) (0.4 g) under stirring and ice-cooling and then stirred for 30 minutes under ice-cooling. Thus obtained solution was added to a solution, which was prepared by stirring a mixture of 7-amino-3-(1-allyl-1H-tetrazol-5-yl)thiomethyl-3-cephem-4-carboxylic acid (0.76 g) and trimethylsilylacetamide (2.3 g) in ethyl acetate (20 ml), under cooling to −25° C. The mixture was stirred for 1 hour at −20° C. to −10° C., and a saturated aqueous solution of sodium chloride (100 ml) was added thereto. Thus obtained mixture was adjusted to pH 7.5 with 20% aqueous solution of sodium carbonate, and the aqueous layer was separated. To the aqueous layer was added ethyl acetate, and adjusted to pH 2 with 10% hydrochloric acid, and then extracted with ethyl acetate. The ethyl acetate layer was washed with a saturated aqueous solution of sodium chloride, dried over magnesium sulfate and then evaporated. The residue was pulverized in diethyl ether, collected by filtration and then dried to give 7-[2-methoxyimino-2-(4-thiazolyl)-acetamido]-3-(1-allyl-1H-tetrazol-5-yl)thiomethyl-3-cephem-4-carboxylic acid (syn isomer) (1.01 g).

IR (Nujol): 3150, 1780, 1720, 1680, 1550 cm$^{-1}$.

NMR (d$_6$-DMSO, δ): 3.67 (2H, broad s), 3.87 (3H, s), 4.32 (2H, AB$_q$, J=13 Hz), 4.77–5.50 (5H, m), 5.57–6.17 (1H, m), 5.83 (1H, dd, J=5 and 8 Hz), 7.88 (1H, d, J=2 Hz), 9.12 (1H, d, J=2 Hz), 9.62 (1H, d, J=8 Hz).

The following compounds were obtained according to similar manners to those of the aforesaid examples.

(1) 7-[2-Methoxyimino-2-(4-thiazolyl)acetamido]cephalosporanic acid (syn isomer).

IR (Nujol): 1775, 1715, 1670 cm$^{-1}$.

NMR (d$_6$-DMSO, δ): 2.04 (3H, s), 3.58 (2H, m), 3.94 (3H, s), 4.88 (2H, ABq, J=12 Hz), 5.20 (1H, d, J=5 Hz), 5.87 (1H, dd, J=5 and 8 Hz), 7.97 (1H, d, J=2 Hz), 9.19 (1H, d, J=8 Hz).

(2) 7-[2-Methoxyimino-2-(4-thiazolyl)acetamido]-3-(1,3,4-thiadiazol-2-yl)thiomethyl-3-cephem-4-carboxylic acid (syn isomer).

IR (Nujol): 3150, 1780, 1670, 1550 cm$^{-1}$.

NMR (d$_6$-DMSO, δ): 3.73 (2H, broad s), 3.93 (3H, s), 4.47 (2H, ABq, J=13 Hz), 5.17 (1H, d, J=5 Hz), 5.73 (1H, dd, J=5 and 8 Hz), 7.96 (1H, d, J=2 Hz), 9.10 (1H, d, J=2 Hz), 9.57 (1H, s), 9.63 (1H, d, J=8 Hz).

What we claim is:

1. The compounds of the formula:

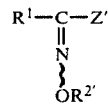

wherein

R$^1$ is 1,2,3-thiadiazolyl, 1,3,4-thiadiazolyl, 1,2,5-thiadiazolyl or isothiazol-4-yl, each of which may be substituted with lower alkyl, or thiazolyl;

R$^{2'}$ is hydrogen, lower alkyl or a hydroxy protective group; and

Z' is carboxy or protected carboxy, and soluble and non-toxic salts thereof.

2. The compounds of claim 1 wherein

R$^1$ is 1,2,3-thiadiazolyl, 1,3,4-thiadiazolyl or 1,2,5-thiadiazolyl,

R$^{2'}$ is lower alkyl, and

Z' is carboxy.

3. The compound of claim 2 which is 2-methoxyimino-2-(1,2,3-thiadiazol-4-yl) acetic acid (syn isomer).

* * * * *